US009476100B1

(12) United States Patent
Frumkin et al.

(10) Patent No.: US 9,476,100 B1
(45) Date of Patent: Oct. 25, 2016

(54) METHODS FOR DIAGNOSING BLADDER CANCER

(71) Applicant: Nucleix Ltd., Rehovot (IL)

(72) Inventors: Danny Frumkin, Tel-Aviv (IL); Adam Wasserstrom, Nes-Ziona (IL)

(73) Assignee: Nucleix Ltd., Rehovot (IL)

( * ) Notice: Subject to any disclaimer, the term of this patent is extended or adjusted under 35 U.S.C. 154(b) by 0 days.

(21) Appl. No.: 14/792,270

(22) Filed: Jul. 6, 2015

(51) Int. Cl.
*C12Q 1/68* (2006.01)
*G06F 19/00* (2011.01)
*A61N 5/10* (2006.01)

(52) U.S. Cl.
CPC .............. *C12Q 1/6886* (2013.01); *A61N 5/10* (2013.01); *G06F 19/345* (2013.01); *C12Q 2600/154* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 6,764,822 B1 | 7/2004 | Butler |
| 6,812,339 B1 | 11/2004 | Venter |
| 2002/0152035 A1 | 10/2002 | Perlin |
| 2004/0181048 A1 | 9/2004 | Wang |
| 2005/0153316 A1 | 7/2005 | Jeddeloh |
| 2005/0272065 A1 | 12/2005 | Lakey |
| 2007/0092883 A1 | 4/2007 | Schouten |
| 2007/0178506 A1 | 8/2007 | Martienssen |
| 2007/0202526 A1 | 8/2007 | Nakami |
| 2007/0207195 A1 | 9/2007 | Yarosh |
| 2007/0275402 A1 | 11/2007 | Lo |
| 2008/0286773 A1 | 11/2008 | Bender |
| 2009/0018031 A1 | 1/2009 | Trinklein et al. |
| 2009/0305234 A1 | 12/2009 | Olek |
| 2012/0003634 A1 | 1/2012 | Frumkin |
| 2013/0078626 A1 | 3/2013 | Wasserstrom |
| 2014/0113286 A1 * | 4/2014 | Chan .................. C12Q 1/6886 435/6.11 |

FOREIGN PATENT DOCUMENTS

| | | |
|---|---|---|
| CA | 2 699 606 A1 | 3/2009 |
| EP | 1213360 | 6/2002 |
| EP | 1748080 | 1/2007 |
| EP | 2071035 A1 | 6/2009 |
| WO | 02/12328 | 2/2002 |
| WO | 2005/040399 | 5/2005 |
| WO | 2007/018601 | 2/2007 |
| WO | 2008/104002 | 8/2008 |
| WO | 2008/140532 A1 | 11/2008 |
| WO | 2009/083989 | 7/2009 |
| WO | 2011/001274 | 1/2011 |
| WO | 2011/070441 | 6/2011 |
| WO | 2011/101728 | 8/2011 |
| WO | 2011/132061 | 10/2011 |
| WO | 2012/070037 | 5/2012 |
| WO | WO 2014193964 A2 * | 12/2014 ............ C12Q 1/6886 |

OTHER PUBLICATIONS

Cacabelos (Epigenetic Biomarkers in Cancer, Clin Med Biochemistry Open Access 1: e101. doi:10.4172/cmbo.1000e101, Nov. 2015).*
Wittenberg et al., (2005) Validation of the high-throughput marker technology DArT using the model plant *Arabidopsis thaliana*. Mol Genet Genomics 274(1): 30-9.
Eads et al., (2000) MethyLight: a high-throughput assay to measure DNA methylation. Nucleic Acids Res 28(8): E32.
Fantappié et al., (2001) Lack of DNA methylation in Schistosoma mansoni. Exp Parasitol 98(3): 162-6.
Frumkin et al., (2010) Authentication of forensic DNA samples. Forensic Sci Int Genet 4(2): 95-103.
Frumkin et al., (2011) DNA methylation-based forensic tissue identification. Forensic Sci Int Genet 5(5): 517-24.
Greiner and Rubocki (2002) Effectiveness of capillary electrophoresis using fluorescent-labeled primers in detecting T-cell receptor gamma gene rearrangements. J Mol Diagn 4(3): 137-43. Abstract only.
Herman et al., (1996) Methylation-specific PCR: a novel PCR assay for methylation status of CpG islands. Proc Natl Acad Sci U S A 93(18): 9821-6.
Holemon et al., (2007) MethylScreen: DNA methylation density monitoring using quantitative PCR. Biotechniques 43(5): 683-93.
Lowe et al., (1990) A computer program for selection of oligonucleotide primers for polymerase chain reactions. Nucleic Acids Res 18(7): 1757-61.
Martin-Magniette et al., (2005) Evaluation of the gene-specific dye bias in cDNA microarray experiments. Bioinformatics 21(9): 1995-2000.
Oakes et al., (2006) Evaluation of a quantitative DNA methylation analysis technique using methylation-sensitive/dependent restriction enzymes and real-time PCR. Epigenetics 1(3):146-52.
Rubin et al., (1994) Alu repeated DNAs are differentially methylated in primate germ cells. Nucleic Acids Res 22(23): 5121-7.
Sakamoto et al., (2007) Cell type-specific methylation profiles occurring disproportionately in CpG-less regions that delineate developmental similarity. Genes Cells 12(10): 1123-32.
Touchman et al., Genebank accession No. G54325.1CBS16 Human EGreen Homo Sapiens STS genomic, sequence tagged site, Aug. 23, 1999 (online). Retrieved on Feb. 20, 2011. Retrieved from the internet: URL: http://www.ncbi.nlm.nih.gov/nuccore/G54325.1.
von Kanel et al., (2010) Quantitative One Step DNA methylation analysis (qOSMA) using native genomic DNA as template (online). Advances in Genomics Jan. 28/29, 2010 (retrieved Nov. 22, 2011), available on the Internet: URL: http://www.advances-ingenomics.org/presentations NonKanel.pdf.

(Continued)

*Primary Examiner* — Aaron Priest
(74) *Attorney, Agent, or Firm* — Winston & Strawn LLP

(57) ABSTRACT

Methods and kits for identification of bladder cancer in a subject based on alterations in DNA methylation at selected genomic loci are provided.

22 Claims, 2 Drawing Sheets

(56) References Cited

OTHER PUBLICATIONS

Yagi et al., (2008) DNA methylation profile of tissue-dependent and differentially methylated regions (T-DMRs) in mouse promoter regions demonstrating tissue-specific gene expression. Genome Res 18(12): 1969-78.

Yamagata et al., (2009) Aberrant DNA methylation status in human uterine leiomyoma. Mol Hum Reprod 15(4): 259-67.

Nouzova et al., (2004) Epigenomic changes during leukemia cell differentiation: analysis of histone acetylation and cytosine methylation using CpG island microarrays. J Pharmacol Exp Ther 311(3): 968-81.

Zeschnigk et al., (2008) IGF2/H19 hypomethylation in Silver-Russell syndrome and isolated hemihypoplasia. Eur J Hum Genet 16(3): 328-34.

Zhao et al., (2005) Study on the application of parent-of-origin specific DNA methylation markers to forensic genetics. Forensic Sci Int 154(2-3): 122-7.

Hua et al., (2011) "Quantitative methylation analysis of multiple genes using methylation-sensitive restriction enzyme-based quantitative PCR for the detection of hepatocellular carcinoma," Experimental and Molecular Pathology, 91(1):455-60.

Reinert et al., (2011) "Comprehensive Genome Methylation Analysis in Bladder Cancer: Identification and Validation of Novel Methylated Genes and Application of These as Urinary Tumor Markers," Clin Cancer Res, 17(17):5582-92.

Homo sapiens KCNJ2 antisense RNA 1 (head to head) (KCNJ2-AS1), long non-coding RNA. Genebank: NR_036534.1, Nov. 5, 2013 (Nov. 5, 2013). URL: htttps://www.ncbi.nlm.nih.gov/nuccore/303227915; 2 pages.

Homo sapiens potassium voltage-gated channel subfamily J member 2 (KCNJ2), RefSeqGene (LRG_328) on chromosome 17. Genebank: NG_008798.1, Feb. 7, 2016 (Feb. 7, 2016). URL: https://www.ncbi.nlm.nih.gov/nucleotide/209969779?report=genbank&log$=nuclalign&blast_rank=2&RID=VV2JJWYR01R; 6 pages.

* cited by examiner

METHODS FOR DIAGNOSING BLADDER CANCER

FIELD OF THE INVENTION

The present invention relates to methods for identifying bladder cancer in a subject by analyzing a biological sample derived therefrom. More particularly, the present invention relates to identification of bladder cancer by analyzing DNA from urine samples. The methods are based on differences in DNA methylation between normal and bladder cancer DNA.

BACKGROUND OF THE INVENTION

Bladder cancer is a cancer arising from cells in the urinary bladder. Most bladder cancers are transitional cell carcinomas, arising from epithelial cells in the inner lining of the bladder (urothelium). Other types of bladder cancers include squamous cell carcinomas, adenocarcinomas, sarcomas and small cell carcinomas.

Diagnosis of bladder cancer is commonly performed by cystoscopy, in which the bladder is examined visually using an endoscope (cystoscope). A biopsy is usually taken from areas of suspicious abnormalities to check for the presence of any cancerous cells.

Another method employed in the diagnosis of bladder cancer is urine cytology, in which a urine sample is analyzed under a microscope to detect the presence of cancer cells. Various imaging methods, such as X-ray and Computed Tomography (CT) have also been utilized for diagnosing bladder cancer, some of which involve injecting a dye intravenously to enable the visualization of the examined tissue.

In recent years, additional diagnostic means for bladder cancer have become available, such as urinary antigen tests and an assay for detecting chromosomal abnormalities in urine samples (UroVysion™).

The currently available methods have a number of drawbacks, as some of them are invasive, laborious and time consuming, and some are insufficiently sensitive and specific. In addition, diagnosis by pathological examination is carried out manually and is therefore subjective. Subjective results are problematic because there can be differences between results of the same sample analyzed by different pathologists, and even by the same pathologist in different times.

WO 2011/001274 and WO 2011/070441, assigned to the Applicant of the present invention, disclose methods for identifying DNA from a natural source and methods for categorization of DNA samples into different types of tissue, respectively, based on ratios of methylation levels at specific genomic loci.

There is an unmet need for improved methods and kits for diagnosing bladder cancer in subjects in need thereof, with high specificity and high sensitivity which do not require well-trained pathologists. There is further a need for objective, user-independent diagnostic methods.

SUMMARY OF THE INVENTION

The present invention provides according to some aspects methods and kits for identification of bladder cancer in subjects in need thereof by analyzing DNA from urine samples. The methods and kits of the present invention are based on methylation differences at selected genomic loci between normal DNA and bladder cancer DNA.

More particularly, the methods and kits of the present invention utilize a set of genomic loci that unexpectedly were found to be highly methylated in DNA derived from bladder cancer, and not in DNA derived from a healthy bladder tissue, and thereby may be used in determining whether a given bladder DNA sample is from a bladder cancer patient or from a healthy subject.

According to the methods and kits of the present invention, DNA from a urine sample of a tested subject is digested with at least one methylation-sensitive restriction enzyme that cleaves its recognition sequence only if it is unmethylated. The set of genomic loci disclosed herein, denoted "restriction loci", contain the recognition sequence of the at least one methylation-sensitive restriction enzyme and are therefore cut (digested) according to their methylation level, where higher methylation results in less digestion by the enzyme. Unexpectedly, a DNA sample from a healthy individual is cut, at the set of genomic loci disclosed herein, more extensively then a DNA sample from a cancer patient. Accordingly, the difference in digestion efficiency between a DNA sample in which the restriction loci of the invention are highly methylated and a DNA sample in which these loci have low methylation levels establishes different amplification patterns in subsequent amplification and quantification steps. Surprisingly, the difference in the amplification patterns allows distinguishing between DNA from bladder cancer tissue and DNA from normal bladder tissue.

The amplification and quantification steps according to the methods and kits of the present invention involve co-amplification of at least one restriction locus and a control locus from the digested DNA. The control locus may be a locus that is not cut by the methylation-sensitive restriction enzyme used in the digestion step. Signal intensities of the amplified loci are then determined, and a ratio is calculated between the signal intensities of each restriction locus and the control locus. It is now disclosed for the first time that distinct signal ratios are produced for bladder cancer DNA and normal bladder DNA, thus enabling identification of bladder cancer.

The identification of bladder cancer is performed by comparing signal ratios calculated for DNA from a tested subject to one or more reference ratios determined for the same restriction loci in known sources, i.e., normal individuals and/or cancer patients. Based on the comparison, the tested sample is identified as derived from a cancer patient or from a healthy subject. It should be noted that at no point the kits and methods of the invention require determination of methylation level of individual loci per se.

The methods and kits of the present invention enable identification of bladder cancer by testing urine samples, thus advantageously providing non-invasive molecular-based diagnosis of the disease. Another benefit of the claimed methods and kits is that identification may be carried out in a urine sample despite relatively low amounts of DNA that urine samples may contain. Additional benefit conferred by diagnosing bladder cancer by the methods and kits disclosed herein is the high sensitivity and specificity of the diagnosis. In addition, the methodology described herein produces an objective result which is not user-dependent.

According to one aspect, the present invention provides a method for identifying bladder cancer in a human subject, the method comprising:

(a) applying DNA from a urine sample obtained from the subject to digestion by at least one methylation-sensitive restriction endonuclease to obtain restriction endonuclease-treated DNA;

(b) co-amplifying from the restriction endonuclease-treated DNA at least one restriction locus comprising the locus set forth in SEQ ID NO: 1 and a control locus, thereby generating an amplification product for each locus;

(c) determining a signal intensity for each generated amplification product;

(d) calculating a ratio between the signal intensities of the amplification products of each of said at least one restriction locus and the control locus; and (e) detecting a high probability score for said ratio with respect to corresponding bladder cancer reference ratio, thereby identifying bladder cancer in the human subject.

In some embodiments, detecting a high probability score for said ratio with respect to corresponding bladder cancer reference ratio comprises detecting a probability score with respect to bladder cancer reference ratio that is above a predefined threshold.

In some embodiments, the at least one restriction locus further comprises the locus set forth in SEQ ID NO: 5, and said probability score is a combined probability score for a SEQ ID NO: 1 ratio and a SEQ ID NO: 5 ratio with respect to their corresponding bladder cancer reference ratios.

In some embodiments, the at least one restriction locus further comprises the locus set forth in SEQ ID NO: 7 and the locus set forth in SEQ ID NO: 11, and said probability score is a combined probability score for said SEQ ID NO: 1 ratio, said SEQ ID NO: 5 ratio, a SEQ ID NO: 7 ratio and a SEQ ID NO: 11 ratio with respect to their corresponding bladder cancer reference ratios.

In some embodiments, the at least one restriction locus further comprises at least one additional restriction locus selected from the group of loci set forth in SEQ ID NO: 2, SEQ ID NO: 3, SEQ ID NO: 4, SEQ ID NO: 6, SEQ ID NO: 8, SEQ ID NO: 9, SEQ ID NO: 10, SEQ ID NO: 12, SEQ ID NO: 13, SEQ ID NO: 14 and SEQ ID NO: 15, and said probability score is a combined probability score for said SEQ ID NO: 1, SEQ ID NO: 5, SEQ ID NO: 7 and SEQ ID NO: 11 ratios and at least one additional ratio of said at least one additional restriction locus with respect to their corresponding bladder cancer reference ratios.

In some embodiments, the at least one additional restriction locus comprises all loci set forth in SEQ ID NO: 2, SEQ ID NO: 3, SEQ ID NO: 4, SEQ ID NO: 6, SEQ ID NO: 8, SEQ ID NO: 9, SEQ ID NO: 10, SEQ ID NO: 12, SEQ ID NO: 13, SEQ ID NO: 14 and SEQ ID NO: 15. Thus, in some embodiments, the at least one restriction locus comprises all loci set forth in SEQ ID NOs: 1-15. Each possibility represents a separate embodiment of the present invention.

In some embodiments, the method further comprises: providing a first and second control constructs comprising non-human DNA sequences, wherein the first control construct comprises a DNA sequence devoid of a recognition sequence of the methylation-sensitive restriction endonuclease, and the second control construct comprises a DNA sequence containing a recognition sequence of the methylation-sensitive restriction endonuclease and being completely unmethylated; digesting the first and second control constructs with the methylation-sensitive restriction endonuclease; and amplifying the first and second control constructs; wherein detection of adequate amplification for the first construct concomitant with low or absence of amplification for the second construct is indicative of proper DNA digestion.

In some embodiments, the at least one methylation-sensitive restriction endonuclease is selected from the group consisting of AatII, Acc65I, AccI, AciI, AclI, AfeI, AgeI, ApaI, ApaLI, AscI, AsiSI, AvaI, AvaII, BaeI, BanI, BbeI, BceAI, BcgI, BfuCI, BglI, BmgBI, BsaAI, BsaBI, BsaHI, BsaI, BseYI, BsiEI, BsiWI, BslI, BsmAI, BsmBI, BsmFI, BspDI, BsrBI, BsrFI, BssHII, BssKI, BstAPI, BstBI, BstUI, BstZ17I, Cac8I, ClaI, DpnI, DrdI, EaeI, EagI, EagI-HF, EciI, EcoRI, EcoRI-HF, FauI, Fnu4HI, FseI, FspI, HaeII, HgaI, HhaI, HincII, HincII, HinfI, HinPII, HpaI, HpaII, Hpy166ii, Hpy188iii, Hpy99I, HpyCH4IV, KasI, MluI, MmeI, MspAII, MwoI, NaeI, NacI, NgoNIV, Nhe-HFI, NheI, NlaIV, NotI, NotI-HF, NruI, Nt.BbvCI, Nt.BsmAI, Nt.CviPII, PaeR7I, PleI, PmeI, PmlI, PshAI, PspOMI, PvuI, RsaI, RsrII, SacII, SalI, SalI-HF, Sau3AI, Sau96I, ScrFI, SfiI, SfoI, SgrAI, SmaI, SnaBI, TfiI, TscI, TseI, TspMI, and ZraI. Each possibility represents a separate embodiment of the present invention.

In some embodiments, step (a) is performed using one methylation-sensitive restriction endonuclease. In some embodiments, the methylation-sensitive restriction endonuclease is HhaI.

In some embodiments, the control locus is a locus devoid of a recognition sequence of the methylation-sensitive restriction endonuclease.

In some embodiments, the control locus is the locus set forth in SEQ ID NO: 16.

In some embodiments, step (b) is performed using real-time PCR.

In some embodiments, step (b) is performed using real-time PCR and the method further comprises adding fluorescent probes for specifically detecting the amplification products of the at least one restriction locus and the at least one control locus.

In some embodiments, step (b) is performed using real-time PCR and said calculating a ratio between the signal intensities of the amplification products of each of said at least one restriction locus and the control locus comprises determining the quantification cycle (Cq) for each locus and calculating $2^{(Cq\ control\ locus - Cq\ restriction\ locus)}$. In some embodiments, the corresponding bladder cancer reference ratio is $2^{(Cq\ control\ locus\ in\ a\ reference\ DNA - Cq\ restriction\ locus\ in\ a\ reference\ DNA)}$ wherein the reference DNA is bladder cancer DNA.

In some embodiments, the method further comprises providing healthy reference ratios, between signal intensities of amplification products of the at least one restriction locus and the control locus in DNA derived from healthy subjects. In some embodiments, the method further comprises detecting a low probability score for said ratio with respect to corresponding healthy reference ratio.

In some embodiments, said bladder cancer is selected from the group consisting of transitional cell carcinoma, squamous cell carcinoma, adenocarcinoma, sarcoma and small cell carcinoma. Each possibility represents a separate embodiment of the present invention.

In some particular embodiments, said bladder cancer is transitional cell carcinoma.

According to yet another aspect, the present invention provides a method of treating bladder cancer in a subject in need thereof, the method comprising identifying bladder cancer according to the method of the present invention, and administering to said subject an anticancer therapy.

In some embodiments, said anticancer therapy comprises one or more of: surgery, radiation therapy, chemotherapy and immunotherapy.

These and further aspects and features of the present invention will become apparent from the detailed description, examples and claims which follow.

DETAILED DESCRIPTION OF THE INVENTION

Figure 1:
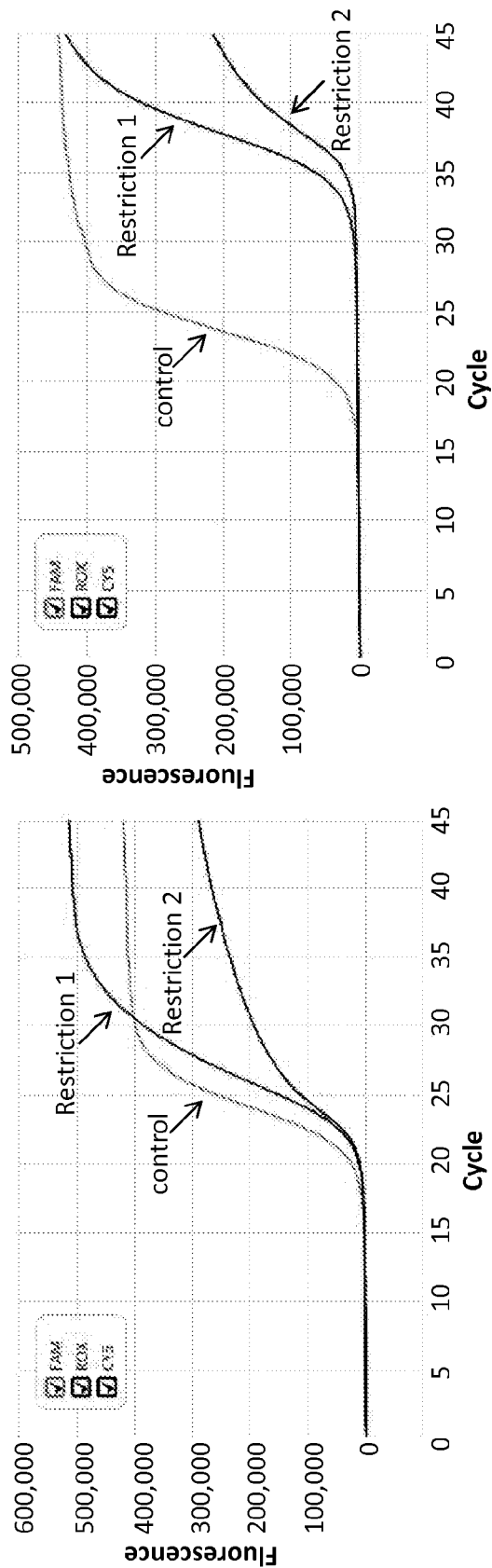
FIG. 1 exhibits exemplary amplification plots of a control locus and two restriction loci in a sample from a cancer patient (left) and a healthy sample (right).

The present invention relates to identification of bladder cancer using DNA from urine samples based on detection of alterations in DNA methylation at predetermined loci.

The present invention involves calculating signal intensity ratios between selected loci co-amplified from a tested DNA sample following digestion of the DNA with at least one methylation sensitive restriction enzyme, and comparing these ratios to one or more reference ratios obtained from a plurality of DNA samples derived from a known source, healthy or bladder cancer. Based on the comparison, the tested sample is identified as derived from a cancer patient or from a healthy subject.

The term "plurality" as used herein refers to 'at least two' or 'two or more'.

The methods of the present invention are particularly beneficial, as they provide highly sensitive and specific means for diagnosing bladder cancer which are non-invasive, user-independent, and may be carried out even in urine samples that contain relatively low amounts of DNA.

Furthermore, in contrast to conventional methods utilizing methylation analysis for distinguishing between cancerous and normal tissues, which require determining actual methylation levels at specific genomic loci, the methodology described herein does not require to evaluate absolute methylation levels. The method disclosed herein therefore eliminates the need for standard curves and/or additional laborious steps involved in determination of methylation levels per se, thereby offers a simple and cost effective procedure. An additional advantage over approaches for analyzing methylation is conferred by the signal ratios obtained by the method of the invention, which are calculated between loci amplified from the same DNA template in the same reaction mixture (i.e., under the same reaction conditions). This renders the method insensitive to various "noise" factors, such as changes in template DNA concentration, PCR conditions, and presence of inhibitors. Such noises are inherent for existing methods that are based on quantifying methylation levels of loci by comparing signals from separate amplification reactions.

In some embodiments, there is provided a method for identifying bladder cancer in a subject, the method comprising: (a) digesting DNA from a urine sample obtained from the subject with at least one methylation-sensitive restriction endonuclease; (b) amplifying at least the restriction locus set forth in SEQ ID NO: 1 and a control locus in the digested DNA sample, wherein the control locus is a locus exhibiting the same digestion and amplification profile in bladder cancer DNA and in healthy DNA, thereby generating an amplification product for each locus in said DNA sample; (c) determining a signal intensity for each generated amplification product; (d) calculating a ratio between the signal intensities of the amplification products of the at least one restriction locus and the control locus in said DNA sample; and (e) detecting a high probability score for said ratio with respect to corresponding bladder cancer reference ratio, thereby identifying bladder cancer in the human subject.

In some embodiments, detecting a high probability score for said ratio with respect to corresponding bladder cancer reference ratio comprises detecting a probability score that is above a predefined threshold.

In some embodiments, detecting a high probability score with respect to bladder cancer reference ratio comprises comparing the ratio to corresponding bladder cancer reference ratio and optionally to healthy reference ratio, and assigning a probability score based on the comparison, wherein a high probability score is indicative of cancer.

Thus, in some embodiments, the method of the present invention comprises providing bladder cancer reference ratios and, optionally, healthy reference ratios.

In some embodiments, step (e) comprises comparing the ratio to a reference scale comprising ratios determined in bladder cancer patients and in healthy individuals, wherein said probability score is a score assigned to said ratio based on its relative position within the reference scale. In some embodiments, the higher the value of the ratio, the higher the score assigned thereto.

In some embodiments, the method further comprises amplifying in step (b) at least one additional restriction locus, thereby generating an amplification product for the at least one additional restriction locus; and repeating steps (c)-(d) for each additional restriction locus. In some embodiments, in step (e), a plurality of individual probability scores is obtained for a plurality of ratios with respect to their corresponding bladder cancer reference ratios, wherein each ratio is between a distinct restriction locus and the control locus. A combined probability score is calculated based on the plurality of probability scores.

In some embodiments, the combined score may be an average score. In other embodiments, the combined score may be a weighted average of the individual probability scores. In some embodiments, the combined score may be a sum of all individual probability scores. In general, the combined score may include any mathematical or statistic value which represents all individual probability score.

In some embodiments, detecting a high combined probability score identifies bladder cancer in the human subject. In some embodiments, detecting a high combined probability score is detecting a combined probability score that is above a pre-defined threshold.

The terms "DNA from", "DNA derived from", "DNA within" and the like are interchangeable and refer to DNA obtained from a urine sample, DNA isolated from a urine sample or a urine sample as is namely, a urine sample containing DNA, or a DNA sample, therewith. Thus, these terms include, but are not limited to, DNA isolated from a urine sample, a urine sample enriched for DNA, and DNA in a non-manipulated urine sample.

Methylation in the human genome occurs in the form of 5-methyl cytosine and is confined to cytosine residues that are part of the sequence CG, also denoted as CpG dinucleotides (cytosine residues that are part of other sequences are not methylated). Some CG dinucleotides in the human genome are methylated, and others are not. In addition, methylation is cell and tissue specific, such that a specific CG dinucleotide can be methylated in a certain cell and at the same time unmethylated in a different cell, or methylated in a certain tissue and at the same time unmethylated in different tissues. DNA methylation is an important regulator of gene transcription. Aberrant DNA methylation patterns, both hypermethylation and hypomethylation compared to normal tissue, have been associated with a large number of human malignancies.

The term "bladder cancer" refers to cancer arising from cells in the urinary bladder. Bladder cancer is used herein to include transitional cell carcinoma (TCC, also referred to as urothelial cell carcinoma), squamous cell carcinoma, adenocarcinoma, small cell carcinoma and sarcoma. Each possibility represents a separate embodiment of the present invention.

TCC, arising from epithelial cells in the inner lining of the bladder (urothelium), is the most common type of bladder cancer accounting for more than 90% of the cases. TCC typically includes two sub-types, papillary carcinomas, in which the tumors grow in slender, finger-like projections from the inner surface of the bladder toward the hollow center, and flat carcinomas, in which tumors do not grow toward the hollow part of the bladder. Squamous cell carcinoma and adenocarcinoma are less common types of bladder cancer, and small cell carcinoma and sarcoma are relatively rare.

Bladder cancer may be typically further classified as either non-invasive, where the cancer cells are confined to the inner layer of the transitional epithelium, or invasive, where cancer cells grow into the lamina propria of the bladder or even deeper into the muscle layer. A bladder cancer can also be described as superficial or non-muscle invasive. These terms include both non-invasive tumors as well as any invasive tumors that have not grown into the main muscle layer of the bladder.

The terms "identification of bladder cancer", "identifying bladder cancer in a subject" and "identifies the subject as having bladder cancer" as used herein are interchangeable and encompass any one or more of screening for bladder cancer, detecting the presence of bladder cancer, detecting recurrence of bladder cancer, detecting susceptibility to bladder cancer, detecting resistance to treatment of bladder cancer, detecting efficacy of treatment to bladder cancer, determining stage (severity) of bladder cancer, determining prognosis of bladder cancer and early diagnosis of bladder cancer in a subject. Each possibility represents a separate embodiment of the present invention.

The term "subject" as used herein is interchangeable with "individual" and refers to a human subject. The subject may be suspected of having bladder cancer. In some embodiments, the subject may be at risk of developing bladder cancer, for example, based on previous history of the disease, genetic predisposition, and/or family history, a subject who has been exposed to any one or more of carcinogens, occupational hazard, environmental hazard and/or a subject who exhibits suspicious clinical signs of cancer. In some embodiments, the subject may show at least one symptom or characteristic of bladder cancer, including for example, presence of blood in the urine, change in urination frequency, anemia, general weakness or symptoms of irritation. In other embodiments, the subject may be asymptomatic.

Urine Sample Collection and Processing

In some embodiments, urine samples may be collected from subjects using conventional collection containers or tubes.

In some embodiments, genomic DNA may be extracted from the urine samples according to methods known in the art. Exemplary procedures are described, e.g., in Sambrook et al, Molecular Cloning: A Laboratory Manual, Fourth Ed., Cold Spring Harbor Laboratory Press, Cold Spring Harbor, N.Y., 2012.

DNA Digestion

According to the methods of the present invention, DNA from the urine sample is subjected to digestion with at least one methylation-sensitive restriction endonuclease, for example, with one, two, three methylation-sensitive restriction endonucleases. Each possibility represents a separate embodiment of the present invention.

In some embodiments, the entire DNA that is extracted from the urine sample is used in the digestion step. In some embodiments, the DNA is not quantified prior to being subjected to digestion. In other embodiments, the DNA may be quantified prior to digestion thereof.

A "restriction endonuclease", used herein interchangeably with a "restriction enzyme", refers to an enzyme that cuts DNA at or near specific recognition nucleotide sequences, known as restriction sites.

A "methylation-sensitive" restriction endonuclease is a restriction endonuclease that cleaves its recognition sequence only if it is unmethylated (while methylated sites remain intact). Thus, the extent of digestion of a DNA sample by a methylation-sensitive restriction endonuclease depends on the methylation level, where a higher methylation level protects from cleavage and accordingly results in less digestion.

In some embodiments, the at least one methylation-sensitive restriction endonuclease may be selected from the group consisting of: AatII, Acc65I, AccI, AciI, AclI, AfeI, AgeI, ApaI, ApaLI, AscI, AsiSI, AvaI, AvaII, BaeI, BanI, BbeI, BceAI, BcgI, BfuCI, BglI, BmgBI, BsaAI, BsaBI, BsaHI, BsaI, BseYI, BsiEI, BsiWI, BslI, BsmAI, BsmBI, BsmFI, BspDI, BsrBI, BsrFI, BssHII, BssKI, BstAPI, BstBI, BstUI, BstZ17I, Cac8I, ClaI, DpnI, DrdI, EaeI, EagI, EagI-HF, EciI, EcoRI, EcoRI-HF, FauI, Fnu4HI, FseI, FspI, HaeII, HgaI, HhaI, HincII, HincII, HinfI, HinPII, HpaI, HpaII, Hpy166ii, Hpy188iii, Hpy99I, HpyCH4IV, KasI, MluI, MmeI, MspAlI, MwoI, NaeI, NacI, NgoNIV, Nhe-HFI, NheI, NlaIV, NotI, NotI-HF, NruI, Nt.BbvCI, Nt.BsmAI, Nt.CviPII, PaeR7I, PleI, PmeI, PmlI, PshAI, PspOMI, PvuI, RsaI, RsrII, SacII, SalI, SalI-HF, Sau3AI, Sau96I, ScrFI, SfiI, SfoI, SgrAI, SmaI, SnaBI, TfiI, TscI, TseI, TspMI, and ZraI. Each possibility represents a separate embodiment of the present invention.

In some embodiments, the urine sample may be subjected to digestion with one methylation-sensitive restriction endonuclease. In some particular embodiments, the methylation-sensitive restriction endonuclease may be HhaI.

In some embodiments, DNA digestion may be carried out to complete digestion. In some embodiments, the methylation-sensitive restriction endonuclease may be HhaI, and complete digestion may be achieved following one to two hours incubation with the enzyme at 37° C.

Amplification of Genomic Loci

The terms "genomic locus" or "locus" as used herein are interchangeable and refer to a DNA sequence at a specific position on a chromosome. The specific position may be identified by the molecular location, namely, by the numbers of the starting and ending base pairs on the chromosome. A variant of a DNA sequence at a given genomic position is called an allele. Alleles of a locus are located at identical sites on homologous chromosomes. Loci include gene sequences as well as other genetic elements (e.g., intergenic sequences).

A "restriction locus" is used herein to describe a locus that contains the recognition sequence of a methylation-sensitive restriction enzyme that is used in the method.

A "control locus" and "internal reference locus" are interchangeable and used herein to describe a locus the digestion of which, with the restriction enzyme applied in the digestion step, is independent of the presence or absence of cancer. In some embodiments, the control locus is a locus that exhibits the same digestion and amplification profile in bladder cancer and in healthy tissue. In some embodiments, the control locus is a locus devoid of the recognition sequence of the restriction enzyme applied in the digestion step. Advantageously, the control locus is an internal locus, i.e. a locus within the analyzed DNA sample, thus eliminating the need for external/additional control sample(s).

In some embodiments, the restriction locus or restriction loci include any one or more of the loci set forth in SEQ ID NOs: 1-15, as follows:

SEQ ID NO: 1, corresponds to position 65676359-65676418 on chromosome 17, (KCNJ2 gene);

SEQ ID NO: 2, corresponds to position 21958446-21958585 on chromosome 9, (CDKN2A gene);

SEQ ID NO: 3, corresponds to position 336844-336903 on chromosome 6, (IRF4 gene); SEQ ID NO: 4, corresponds to position 33319507-33319636 on chromosome 21, (Olig2 gene);

SEQ ID NO: 5, corresponds to position 166502151-166502220 on chromosome 6, intergenic region;

SEQ ID NO: 6, corresponds to position 896902-897031 on chromosome 18, (ADCYAP1 gene);

SEQ ID NO: 7, corresponds to position 32747873-32748022 on chromosome 5, (NPR3 gene);

SEQ ID NO: 8, corresponds to position 27949195-27949264 on chromosome 6, intergenic region;

SEQ ID NO: 9, corresponds to position 27191603-27191672 on chromosome 7, (HOXA9 gene);

SEQ ID NO: 10, corresponds to position 170170302-170170361 on chromosome 16, intergenic region;

SEQ ID NO: 11, corresponds to position 30797737-30797876 on chromosome 15, intergenic region;

SEQ ID NO: 12, corresponds to position 7936767-7936866 on chromosome 1, intergenic region;

SEQ ID NO: 13, corresponds to position 170077565-170077634 on chromosome 1, (DNM3 gene);

SEQ ID NO: 14, corresponds to position 1727592-1727661 on chromosome 2, (PXDN gene); and SEQ ID NO: 15, corresponds to position 72919092-72919231 on chromosome 8, (MSC gene).

Unexpectedly, the restriction loci set forth in SEQ ID NOs: 1-15 were identified by the inventors of the present invention to be differentially methylated between cancerous bladder tissue and normal bladder tissue. More particularly, these loci have increased methylation in bladder cancer tissue compared to normal tissue.

Each of these loci contains CG dinucleotides that are more methylated in DNA from cancerous bladder tissue compared to DNA from normal non-cancerous bladder tissue. Advantageously, the differentially methylated CG dinucleotides are located within recognition sites of methylation-sensitive restriction enzymes.

In some embodiments, each of these loci may contain at least one restriction site of a methylation-sensitive restriction enzyme in which the CG dinucleotide is more methylated in bladder cancer cells than in normal cells, meaning that in the cancerous tissue a greater number of cells contain methylation at this position compared to normal tissue. In some embodiments, each of these loci may contain at least one HhaI restriction site (GCGC). The methylation-sensitive restriction enzyme cleaves its recognition sequence only if it is unmethylated. Thus, a DNA sample containing a higher percentage of DNA molecules in which the CG dinucleotide in the restriction site is methylated would be digested to a lesser extent compared to a DNA sample containing a higher percentage of DNA molecules in which the CG dinucleotide is unmethylated. Based on the methods disclosed herein, DNA digestion by methylation-sensitive restriction enzymes is less extensive for DNA from urine samples of bladder cancer patients compared to DNA from normal (healthy) individuals. It was surprisingly found that the difference in digestion efficiency establishes different amplification patterns in subsequent amplification and quantification steps, which enables distinguishing between DNA from a cancerous bladder tissue and DNA from a normal bladder tissue.

In some embodiments, each of the loci set forth in SEQ ID NOs: 1-15 may contain additional CG dinucleotides whose methylation status is of no relevance or influence on the assay—only methylation at the recognition sequence of the restriction enzyme (e.g. HhaI) is relevant.

In some embodiments, the control locus is as set forth in SEQ ID NO: 16, which corresponds to position 121380854-121380913 on chromosome 7 (intergenic region). In some embodiments, the control locus, also termed an internal reference locus, does not contain a recognition sequence of the restriction enzyme. In some embodiment, the sequence of the control locus remains intact (regardless of its methylation status) when a DNA sample is digested with a methylation-sensitive restriction enzyme.

In some embodiments, the sequence of the control locus exhibits the same digestion and amplification profile in bladder cancer tissue and in a healthy bladder tissue.

In some embodiments, the control locus comprises the locus set forth in SEQ ID NO: 16 and the amplification pattern of the control locus following digestion with the methylation sensitive restriction enzyme is not affected by methylation.

The advantage in using the restriction loci set forth in SEQ ID NOs: 1-15 for differentiating between urine samples of bladder cancer patients and those of healthy individuals is exemplified herein below using the methylation sensitive restriction enzyme HhaI. Amplification of each of these restriction loci and the control locus set forth in SEQ ID NO: 16 following digestion with HhaI was carried out in large groups of cancer patients and healthy individuals. Calculation of signal ratios between the amplification products of each restriction locus and the control locus showed significantly higher mean signal ratios (at least one order of magnitude higher) in the cancer group compared to the control group.

In some embodiments, the method comprises amplifying at least one restriction locus and at least one genomic locus following digestion of the DNA sample.

As used herein, "at least one (restriction/control) locus", may encompass a single locus or a plurality of separate loci, such that, a phrase like "at least one restriction locus comprising the locus set forth in SEQ ID NO: 1 and the locus set forth in SEQ ID NO: 2" indicates that at least these two separate genomic loci are amplified.

In some embodiments, the method comprises amplifying the restriction locus set forth in SEQ ID NO: 1 and a control locus, and optionally at least one additional restriction locus.

In some embodiments, the method comprises amplifying a restriction locus as set forth in SEQ ID NO: 1 and a control locus as set forth in SEQ ID NO: 16.

In some embodiments, the method comprises amplifying a plurality of restriction loci (i.e., at least two restriction loci) and a control locus.

In some embodiments, the plurality of restriction loci comprises a restriction locus as set forth in SEQ ID NO: 1 and a restriction locus as set forth in SEQ ID NO: 5. In some embodiments, the method comprises amplifying a first restriction locus as set forth in SEQ ID NO: 1 and further comprises amplifying a second restriction locus as set forth in SEQ ID NO: 5.

In some embodiments, the plurality of restriction loci further comprises at least one restriction locus selected from the loci set forth in SEQ ID NO: 7 and SEQ ID NO: 11. In some embodiments, the plurality of restriction loci further comprises a third and fourth restriction loci as set forth in SEQ ID NOs: 7 and 11, respectively.

In some embodiments, the plurality of restriction loci further comprises at least one additional restriction locus selected from the group consisting of SEQ ID NO: 2, SEQ ID NO: 3, SEQ ID NO: 4, SEQ ID NO: 6, SEQ ID NO: 8, SEQ ID NO: 9, SEQ ID NO: 10, SEQ ID NO: 12, SEQ ID NO: 13, SEQ ID NO: 14 and SEQ ID NO: 15. Each possibility represents a separate embodiment of the present invention.

In some embodiments, the plurality of restriction loci comprises the locus set forth as SEQ ID NO: 1 and further comprises one, two, three, four, five, six, seven, eight, nine, ten, eleven, twelve, thirteen or fourteen additional restriction loci selected from the group consisting of SEQ ID NOs: 2-15. Each possibility represents a separate embodiment of the present invention.

In some embodiments, the plurality of restriction loci comprises the loci set forth as SEQ ID NOs: 1 and 5, and further comprises one, two, three, four, five, six, seven, eight, nine, ten, eleven, twelve or thirteen additional restriction loci selected from the group consisting of SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15. Each possibility represents a separate embodiment of the present invention.

In some embodiments, the plurality of restriction loci comprises the loci set forth as SEQ ID NOs: 1, 5 and 7, and further comprises one, two, three, four, five, six, seven, eight, nine, ten, eleven or twelve additional restriction loci selected from the group consisting of SEQ ID NO: 2, SEQ ID NO: 3, SEQ ID NO: 4, SEQ ID NO: 6, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15. Each possibility represents a separate embodiment of the present invention.

In some embodiments, the plurality of restriction loci comprises the loci set forth as SEQ ID NOs: 1, 5, 7 and 11, and further comprises one, two, three, four, five, six, seven, eight, nine, ten or eleven additional restriction loci selected from the group consisting of SEQ ID NO: 2, SEQ ID NO: 3, SEQ ID NO: 4, SEQ ID NO: 6, SEQ ID NO: 8, SEQ ID NO: 9, SEQ ID NO: 10, SEQ ID NO: 12, SEQ ID NO: 13, SEQ ID NO: 14 and SEQ ID NO: 15. Each possibility represents a separate embodiment of the present invention.

In some embodiments, the plurality of restriction loci comprises the restriction loci set forth in SEQ ID NOs: 1-15. In some embodiments, the plurality of restriction loci is consisting of the restriction loci set forth in SEQ ID NOs: 1-15. In some embodiments, the method comprises amplifying a plurality of restriction loci as set forth SEQ ID NOs: 1-15.

As used herein, "amplification" refers to an increase in the number of copies of one or more particular nucleic acid target of interest. Amplification is typically performed by polymerase chain reaction (PCR) in the presence of a PCR reaction mixture which may include a suitable buffer supplemented with the DNA template, polymerase (usually Taq Polymerase), dNTPs, primers and probes (as appropriate), as known in the art.

The term "polynucleotide" as used herein include polymeric forms of nucleotides of any length, either deoxyribonucleotides or ribonucleotides, or analogs thereof. The term "oligonucleotide" is also used herein to include a polymeric form of nucleotides, typically of up to 100 bases in length.

An "amplification product" collectively refers to nucleic acid molecules of a particular target sequence that are generated and accumulated in an amplification reaction. The term generally refers to nucleic acid molecules generated by PCR using a given set of amplification primers.

As used herein, a "primer" defines an oligonucleotide which is capable of annealing to (hybridizing with) a target sequence, thereby creating a double stranded region which can serve as an initiation point for DNA synthesis under suitable conditions. The terminology "primer pair" refers herein to a pair of oligonucleotides which are selected to be used together in amplifying a selected nucleic acid sequence by one of a number of types of amplification processes, preferably PCR. As commonly known in the art, the primers may be designed to bind to a complementary sequence under selected conditions.

The primers may be of any suitable length, depending on the particular assay format and the particular needs. In some embodiments, the primers may include at least 15 nucleotides in length, preferably between 19-25 nucleotides in length. The primers may be adapted to be especially suited to a chosen nucleic acid amplification system. As commonly known in the art, the oligonucleotide primers may be designed by taking into consideration the melting point of hybridization thereof with their targeted sequence (Sambrook et al, ibid).

In some embodiments, the restriction and control loci may be amplified from the same DNA sample (the digested sample) using pairs of reverse and forward primers designed as known in the art to specifically amplify each locus. In some embodiments, the primers may be designed to amplify a locus along with 5' and 3' flanking sequences thereof.

In some embodiments, the 5' flanking sequences may include between 1-60 bases. In additional embodiments, the 5' flanking sequences are of between 10-50 bases. For example, the 5' flanking sequences may include 10 bases, 15 bases, 20 bases, 25 bases, 30 bases, 35 bases, 40 bases, 45 bases, or 50 bases immediately upstream of the locus. Each possibility represents a separate embodiment of the present invention.

In some embodiments, the 3' flanking sequences may include between 1-90 bases. In some embodiments, the 3' flanking sequences may include between 5-80 bases. In some embodiments, the 3' flanking sequences may include 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 bases immediately downstream of the locus. Each possibility represents a separate embodiment of the present invention.

In some embodiments, the primers may be designed to generate amplification products of between 75-225 bases in length.

In some embodiments, the method involves simultaneous amplification of more than one target sequence (at least one restriction locus and one control locus) in the same reaction mixture, a process known as multiplex amplification or co-amplification. This process requires simultaneous use of multiple primer pairs. As known in the art, the primers may be designed such that they can work at the same annealing temperature during amplification. In some embodiments, primers with similar melting temperature (Tm) are used in the method disclosed herein. A Tm variation of between about 3°-5° C. is considered acceptable for primers used in a pool.

In some embodiments, all restriction and control loci may be amplified in a single reaction mixture. In other embodiments, for example due to technical limitation of a particular machine, the digested DNA sample may be divided into several aliquots, each of which is supplemented with primer pairs for amplification of one or more restriction loci and the control locus. Thus, even if a DNA sample is divided into several aliquots, the control locus is amplified in each aliquot, and calculation of signal ratios is performed for the control locus and a restriction locus that are amplified together, i.e., from the same aliquot.

In some embodiments, the method may use control constructs comprising non-human DNA sequences in the digestion and amplification step(s). In some embodiments, the control constructs comprise artificial (synthetic) DNA sequences. The control constructs may be used for controlling the digestion and amplification processes, for example, monitoring the efficacy and quality of the digestion and amplification steps. In some embodiments, the control constructs and the DNA sample are digested, by the at least one methylation-sensitive restriction enzyme, at the same time, and optionally, within the same container (e.g. test tube, vial and the like). In some embodiments, the method may include the step of subjecting the control constructs to digestion with the at least one methylation-sensitive restriction enzyme, together with the DNA sample. In some embodiments, the method may include adding the control constructs to the DNA sample and subjecting both to digestion with the at least one methylation-sensitive restriction enzyme.

In some embodiments, a methylation-sensitive restriction endonuclease may be used in the digestion step, together with one or more of the following control constructs: a first control construct comprising a DNA sequence devoid of a recognition sequence of the methylation-sensitive restriction endonuclease, and a second control construct comprising a DNA sequence containing a recognition sequence of the methylation-sensitive restriction endonuclease and being completely unmethylated, such that, the first control construct remains intact, whereas the second control construct is digested completely, or at least partially. In the subsequent amplification steps, primers (and optionally probes) which are specific for the control constructs may be added. Detection of adequate amplification for the first construct concomitant with sufficiently lower amplification for the second construct is indicative of proper DNA digestion.

In some embodiments, detecting adequate amplification for the first construct concomitant with sufficiently lower amplification for the second construct may include detecting a difference of at least 5 cycles between quantification cycles (Cq) of the first and second control constructs in Real-Time PCR. In some embodiments, the difference may be of at least 6 cycles, at least 7 cycles or at least 8 cycles. Each possibility represents a separate embodiment of the present invention.

In some embodiments, the first and second control constructs may include SEQ ID NOs: 17 and 18, respectively. In some embodiments, primers and probes for amplifying and detecting the first control construct may include SEQ ID NO: 19 (forward), SEQ ID NO: 20 (reverse) and SEQ ID NO: 21 (probe). In some embodiment, primers and probes for amplifying and detecting the second control construct may include SEQ ID NO: 22 (forward), SEQ ID NO: 23 (reverse) and SEQ ID NO: 24 (probe).

In some embodiments, amplification of the genomic loci may be carried out using Real-Time PCR (RT-PCR), also known as quantitative PCR (qPCR), in which simultaneous amplification and detection of the amplification products are performed.

In some embodiments, detection of the amplification products in RT-PCR may be achieved using polynucleotide probes, typically fluorescently-labeled polynucleotide probes.

As used herein, "polynucleotide probes" or "oligonucleotide probes" are interchangeable and refer to labeled polynucleotides which are complementary to specific sub-sequences within the nucleic acid sequences of loci of interest, for example, within the sequence of a restriction locus or a control locus. In some embodiments, detection is achieved by using TaqMan assays based on combined reporter and quencher molecules (Roche Molecular Systems Inc.). In such assays, the polynucleotide probes have a fluorescent moiety (fluorophore) attached to their 5' end and a quencher attached to the 3' end. During PCR amplification, the polynucleotide probes selectively hybridize to their target sequences on the template, and as the polymerase replicates the template it also cleaves the polynucleotide probes due to the polymerase's 5'-nuclease activity. When the polynucleotide probes are intact, the close proximity between the quencher and the fluorescent moiety normally results in a low level of background fluorescence. When the polynucleotide probes are cleaved, the quencher is decoupled from the fluorescent moiety, resulting in an increase of intensity of fluorescence. The fluorescent signal correlates with the amount of amplification products, i.e., the signal increases as the amplification products accumulate.

As used herein, "selectively hybridize to" (as well as "selective hybridization," "specifically hybridize to," and "specific hybridization") refers to the binding, duplexing, or hybridizing of a nucleic acid molecule (such as a primer or a probe) preferentially to a particular complementary nucleotide sequence under stringent conditions. The term "stringent conditions" refers to conditions under which a nucleic acid molecule will hybridize preferentially to its target sequence and to a lesser extent to, or not at all to, other non-target sequences. A "stringent hybridization" in the context of nucleic acid hybridization is sequence-dependent, and differs under different conditions, as known in the art.

Polynucleotide probes may vary in length. In some embodiments, the polynucleotide probes may include between 15-30 bases. In additional embodiments, the polynucleotide probes may include between 25-30 bases. In some embodiments, the polynucleotide probes may include between 20-30 bases, for example, 20 bases, 21 bases, 22 bases, 23 bases, 24 bases, 25 bases, 26 bases, 27 bases, 28 bases, 29 bases, 30 bases. Each possibility represents a separate embodiment of the present invention.

Polynucleotide probes may be designed to bind to either strand of the template. Additional considerations include the Tm of the polynucleotide probes, which should preferably be compatible to that of the primers. Computer software may be used for designing the primers and probes.

As noted above, the methods disclosed herein may involve simultaneous amplification of more than one target sequence (at least one restriction locus and one control locus) in the same reaction mixture. In order to distinguish between multiple target sequences that are amplified in parallel, polynucleotide probes labeled with distinct fluorescent colors may be used.

In some embodiments, the polynucleotide probes form a fluorophore/quencher pairs as known in the art and include, for example, FAM-TAMRA, FAM-BHQ1, Yakima Yellow-BHQ1, ATTO550-BHQ2 and ROX-BHQ2.

In some embodiments, the dye combinations may be compatible to the RT-PCR thermocycler of choice.

In some embodiments, fluorescence may be monitored during each PCR cycle, providing an amplification plot showing the change of fluorescent signals from the probes as a function of cycle number.

In the context of RT-PCR, the following terminology is used:

"Quantification cycle" ("Cq") refers to the cycle number in which fluorescence increases above a threshold, set automatically by software or manually by the user. In some embodiments, the threshold may be constant for all loci and may be set in advance, prior to carrying out the amplification and detection. In other embodiments, the threshold may be defined separately for each locus after the run, based on the maximum fluorescence level detected for this locus during the amplification cycles.

"Threshold" refers to a value of fluorescence used for Cq determination. In some embodiments, the threshold value may be a value above baseline fluorescence, and/or above background noise, and within the exponential growth phase of the amplification plot.

"Baseline" refers to the initial cycles of PCR where there is little to no change in fluorescence.

Computer software may be used to analyze amplification plots and determine baseline, threshold and Cq.

Following digestion with the at least one methylation-sensitive restriction enzyme, loci in which the CG dinucleotide in the enzyme's recognition site is methylated are amplified with high efficiency, because the DNA molecules are protected from digestion. The result is relatively low Cq values because detectable amplification products are shown following a relatively small (low) number of amplification cycles. Conversely, loci in which the CG dinucleotide in the enzyme's recognition site is unmethylated are cut more extensively during the digestion step, and thus result in higher Cq values in the amplification and quantification step (i.e., show detectable amplification products following a relatively high number of amplification cycles).

In alternative embodiments, amplification and detection of amplification products may be carried out by conventional PCR using fluorescently-labeled primers followed by capillary electrophoresis of amplification products. In some embodiments, following amplification the amplification products are separated by capillary electrophoresis and fluorescent signals are quantified. In some embodiments, an electropherogram plotting the change in fluorescent signals as a function of size (bp) or time from injection may be generated, wherein each peak in the electropherogram corresponds to the amplification product of a single locus. The peak's height (provided for example using "relative fluorescent units", rFU) may represent the intensity of the signal from the amplified locus. Computer software may be used to detect peaks and calculate the fluorescence intensities (peak height) of a set of loci whose amplification products were run on the capillary electrophoresis machine, and subsequently the ratios between the signal intensities.

For DNA samples digested with a methylation-sensitive restriction enzyme, e.g., HhaI, loci in which the CG dinucleotide in the enzyme's recognition site is methylated produce a relatively strong signal (higher peak) in the electropherogram. Conversely, loci in which the CG dinucleotide in the enzyme's recognition site is unmethylated produce a relatively weak signal (lower peak) in the electropherogram.

In some embodiments, the fluorescent labels of the primers include any one of fluorescein, FAM, lissamine, phycoerythrin, rhodamine, Cy2, Cy3, Cy3.5, Cy5, Cy5.5, Cy7, FluorX, JOE, HEX, NED, VIC and ROX.

Signal Ratio

The term "ratio" or "signal ratio" as used herein refers to the ratio between the intensities of signals obtained from co-amplification of a pair of genomic loci in a single DNA sample (in the same reaction mixture), particularly co-amplification of a restriction locus and a control locus.

As used herein, a "SEQ ID NO: X ratio" refers to the ratio between the signal intensity of the locus set forth in SEQ ID NO: X and the signal intensity of a control locus, following co-amplification of this pair of loci in a DNA sample digested with a restriction enzyme as detailed herein.

The term "signal intensity" as used herein refers to a measure reflecting the amount of locus-specific amplification products corresponding to the initial amount of intact copies of the locus. However, the signal intensity may not indicate actual amounts of amplification products/intact loci, and may not involve calculation of any absolute amounts of amplification products/intact loci. Thus, for calculating ratios of amplicon signals, no standard curve or reference DNA may be needed since it is unnecessary to calculate actual DNA concentrations or DNA methylation level per se.

In some exemplary embodiments, amplification and detection of amplification products are carried out by RT-PCR where the signal intensity of a specific locus may be represented by the Cq calculated for this locus. The signal ratio in this case may be represented by the following calculation: $2^{(Cq\ of\ control\ locus - Cq\ of\ restriction\ locus)}$.

In additional exemplary embodiments, detection of amplification products is carried out by capillary electrophoresis wherein the signal intensity of a specific locus is the number of relative fluorescence units (rfus) of its corresponding peak. The signal ratio may be calculated by dividing the heights of peaks of each restriction locus by the height of the peak of a control locus.

In some embodiments, calculating a ratio between signal intensities of the amplification products of a restriction locus and a control locus in a DNA sample comprises: (i) determining the signal intensity of the amplification product of the restriction locus; (ii) determining the signal intensity of the amplification product of the control locus; and (iii) calculating a ratio between the two signal intensities.

In some embodiments, calculating a ratio between signal intensities of the amplification products of a restriction locus and a control locus in the DNA sample comprises determining the Cq for each locus, and calculating the difference between the Cq of the control locus and the Cq of the restriction locus. In some embodiments, the calculating further comprises applying the following formula: 2^(Cq of control locus−Cq of restriction locus).

In some embodiments, calculating a signal ratio may be calculating a plurality of signal ratios, between each restriction locus and a control locus.

In some embodiments, calculating a signal ratio may be calculating a ratio between the restriction locus set forth in SEQ ID NO: 1 and a control locus.

In some embodiments, a plurality of loci among the loci set forth in SEQ ID NOs: 1-15 are amplified wherein the method comprises calculating ratios between each of the loci set forth SEQ ID NOs: 1-15 and a control locus, e.g., between the locus set forth in SEQ ID NO: 1 and the control locus, between the locus set forth in SEQ ID NO: 2 and the control locus, and so forth.

In some embodiments, computer software may be used for calculating a ratio between signal intensities of amplification products.

Reference Ratio

The terms "reference ratio" or "reference signal ratio" are used interchangeably and refer to a signal intensity ratio determined in DNA from a known source. A reference ratio for a given pair of restriction and control loci may be represented in a number of ways. In some embodiments, the reference ratio for a given pair of loci may be a single ratio. In some embodiments, the reference ratio for a given pair of loci may be a statistic value, such as, the mean value of a large set of reference ratios, obtained from a large set of DNA samples from a known source, e.g., mean value determined in a large group of cancer patients or a mean value determined in a large group of healthy individuals.

In other embodiments, the reference ratio for a given pair of loci may be a plurality of ratios, such as a distribution of ratios determined for this pair of loci in a large set of DNA samples from a known source. In some embodiments, the reference ratio may a reference scale.

In some embodiments, a reference scale for a given pair of loci may include signal ratios measured for this pair of loci in a plurality of DNA samples from the same reference source. For example, a reference scale of reference bladder cancer patients or a reference scale of reference healthy individuals. In other embodiments, a reference scale for a given pair of loci may include signal ratios from both healthy and diseased individuals, i.e. a single scale combining reference ratios from both sources. Generally, when a single scale is used, the values are distributed such that the values from the healthy individuals are at one end of the scale, e.g. below a cutoff, while the values from the cancer patients are at the other end of the scale, e.g., above the cutoff. In some embodiments, a signal ratio calculated for a tested DNA sample from an unknown source may be compared against the reference scale of healthy and cancer reference ratios, and the probability score may be a score assigned to the calculated signal ratio based on its relative position within the scale. In some embodiments, the higher the calculated signal ratio the higher the score assigned thereto, and accordingly the probability with respect to bladder cancer is high.

The terms "bladder cancer reference ratio" or "reference ratio in bladder cancer DNA" interchangeably refer to the signal intensity ratio measured between a given restriction locus and a given control locus in DNA from urine samples of bladder cancer patients. The bladder cancer reference ratio represents the signal intensity ratio in bladder cancer DNA, namely, DNA from a cancerous bladder tissue. The bladder cancer reference ratio may be a single ratio, a statistic value or a plurality of ratio (e.g., distribution), as detailed above.

The terms "healthy reference ratio", "normal reference ratio" or reference ratio in healthy DNA" interchangeably refer to the signal intensity ratio measured between a given restriction locus and a given control locus in urine samples from normal individuals. A "healthy" or "normal" individual is defined herein as an individual without detectable bladder diseases or symptoms, bladder associated diseases including bladder cancer determined by conventional diagnostic methods. The healthy reference ratio represents the signal intensity ratio in normal bladder DNA, namely, DNA from a normal, non-cancerous bladder tissue. The healthy reference ratio may be a single ratio, a statistic value or a plurality of ratio (e.g., distribution), as detailed above.

In some embodiments, the method disclosed herein comprises pre-determination of reference ratios from cancerous bladder DNA. In some embodiments, the method of the present invention comprises pre-determination of reference ratios from normal bladder DNA.

As noted above, a signal ratio may be determined by various methods, including for example measuring peaks following capillary electrophoresis or calculating Cq following RT-PCR. It is to be understood that the reference ratios and ratios measured for a tested sample of an unknown source in order to determine bladder cancer are obtained using the method disclosed herein.

Determining Bladder Cancer

In some embodiments, the method disclosed herein is based on evaluating the signal ratios calculated for DNA from a urine sample of an unknown source compared to reference ratios in order to identify bladder cancer.

In some embodiments, the calculated signal ratios indicate that the DNA is bladder cancer DNA.

A person of skill in the art would appreciate that the comparison of signal ratios calculated for a tested sample to corresponding reference signal ratios may be performed in a number of ways, using various statistical means.

In some embodiments, comparing a test signal ratio calculated for a given pair of loci to a reference signal ratio comprises comparing the test signal ratio against a single reference value. The single reference value may correspond to a mean value obtained for reference signal ratios from a large population of cancer patients or healthy individuals. In other embodiments, comparing a test signal ratio calculated for a given pair of loci to a reference signal ratio comprises comparing the test signal ratio against a distribution, or scale, of a plurality of reference signal ratios.

Known statistical means may be employed in order to determine whether the signal ratio calculated between a given restriction locus and a control locus corresponds to bladder cancer reference ratio or to normal reference ratio. In some embodiments, detecting close approximation of a calculated ratio to bladder cancer reference ratio identifies a subject as a subject having bladder cancer. Conversely, in some embodiments, detecting close approximation of a calculated ratio to normal reference ratio identifies a subject as a subject not having bladder cancer.

In some embodiments, the method comprises comparing a calculated signal ratio to its corresponding bladder cancer reference ratio (i.e., to a signal ratio determined for the same pair of loci in bladder cancer) to obtain a probability score reflecting the likelihood that the calculated signal ratio is a bladder cancer ratio. The better approximation of the calculated signal ratio to the reference ratio, the higher the probability score and accordingly the likelihood that the calculated signal ratio is a bladder cancer ratio. In some embodiments, the probability score is based on the relative position of the calculated signal ratio within the distribution of bladder cancer reference ratios.

In some embodiments, the method comprises comparing a plurality of signal ratios, calculated for a plurality of restriction loci with respect to a control locus, to their corresponding bladder cancer references ratios.

In some embodiments, a pattern of signal ratios may be analyzed using statistical means and computerized algorithm to determine if it represents a pattern of bladder cancer or a normal, healthy pattern. Exemplary algorithms are disclosed, for example, in WO 2011/070441, assigned to the Applicant of the present invention. The algorithms may include, but are not limited to, machine learning and pattern recognition algorithms In some exemplary embodiments, each calculated ratio (for each pair of restriction and control locus) may be compared against a scale of reference ratios generated for this pair from a large set of urine samples from both cancer patients and individuals not afflicted with cancer. The scale may represent signal ratios calculated between the pair of restriction locus and control locus in a large number of samples from cancer patients and normal individuals. The scale may exhibit a threshold value, also termed hereinafter 'cutoff' or 'pre-defined threshold', above which are reference ratios corresponding to bladder cancer and below are reference ratios corresponding to healthy individuals, or the other way around.

In some embodiments, the lower ratios, at the bottom of the scale and/or below a cutoff, may be from samples of normal individuals (healthy, i.e., not afflicted with bladder cancer), while the higher ratios at the top of the scale and/or above a predetermined cutoff, may be from the cancer patients. For each ratio (between each restriction locus and the control locus), a score may be given based on its relative position on the scale, and the individual scores for each locus are combined to give a single score. In some embodiments, the individual scores may be summed to give a single score. In other embodiments, the individual scores may be averaged to give a single score. In some embodiments, the single score may be used for determining whether the subject is having cancer, where a score above a pre-defined threshold is indicative of bladder cancer.

In some embodiments, a score is a number between 0-100 reflecting the probability that the calculated signal ratio is a bladder cancer ratio, wherein 0 being the lowest probability and 100 being the highest probability. In some embodiments, a threshold score is determined, wherein a score equal to or above which is indicative of bladder cancer. The threshold may be, for example, 40, 50, 60 or 70. Each possibility represents a separate embodiment of the present invention.

In additional exemplary embodiments, for each calculated ratio (between each restriction locus and the control locus), the probability that it represents bladder cancer DNA may be determined based on comparison to corresponding bladder cancer reference ratio and normal reference ratio, and a score (probability score) may be allocated. Consequently, the individual probability scores calculated for each ratio (for each locus) are combined (e.g. summed or averaged) to give a combined score. The combined score may be used for determining whether the subject is having cancer, where a combined score above a pre-defined threshold is indicative of bladder cancer.

Thus, in some embodiments, a threshold, or cutoff, score is determined, above (or below) which the subject is identified as having bladder cancer. The threshold score differentiates the population of healthy subjects from the population of non-healthy subject.

In some embodiments, the method of the present invention comprises providing a threshold score.

In some embodiments, determining the threshold score includes measuring signal ratios in a large population of subjects that are either healthy or have bladder cancer.

In some embodiments, the threshold values are statistically significant values. Statistical significance is often determined by comparing two or more populations, and determining a confidence interval (CI) and/or a p value. In some embodiments, the statistically significant values refer to confidence intervals (CI) of about 90%, 95%, 97.5%, 98%, 99%, 99.5%, 99.9% and 99.99%, while preferred p values are less than about 0.1, 0.05, 0.025, 0.02, 0.01, 0.005, 0.001 or less than 0.0001. Each possibility represents a separate embodiment of the present invention. According to some embodiments, the p value of the threshold score is at most 0.05.

As used herein, the term "about", when referring to a measurable value is meant to encompass variations of +/−10%, more preferably +/−5%, even more preferably +/−1%, and still more preferably +/−0.1% from the specified value.

In some embodiments, the method further comprises comparing the signal ratio calculated between a given restriction locus and a control locus to its corresponding normal bladder reference ratio to obtain a probability score, wherein detecting a low probability score for said ratio with respect to corresponding healthy reference ratio is indicative that the subject has bladder cancer.

In some embodiments, the sensitivity of the methods disclosed herein may be at least about 75%. In some embodiments, the sensitivity of the methods may be at least about 80%. In some embodiments, the sensitivity of the method may be at least about 85%. In some embodiments, the sensitivity of the methods may be at least about 90%.

In some embodiments, the "sensitivity" of a diagnostic assay as used herein refers to the percentage of diseased individuals who test positive (percent of "true positives"). Accordingly, diseased individuals not detected by the assay are "false negatives". Subjects who are not diseased and who test negative in the assay are termed "true negatives." The "specificity" of the diagnostic assay is one (1) minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

In some embodiments, the specificity of the methods disclosed herein may be at least about 65%. In some embodiments, the specificity of the methods may be at least about 70%. In some embodiments, the specificity of the method may be at least about 75%. In some embodiments, the specificity of the methods may be at least about 80%.

Bladder Cancer Treatment

In some embodiments, methods for treating bladder cancer are provided, comprising identifying bladder cancer according to the method of the present invention, and administering to said subject anticancer therapy.

Methods for treating bladder cancer may include one or more of: surgery to remove to tumor, parts of the bladder or the entire bladder in more severe cases; radiation therapy (external or internal); chemotherapy (systemic or regional); and immunotherapy, as known in the art. Each possibility represents a separate embodiment of the present invention.

Kits

In some embodiments, there is provided a kit for identification of bladder cancer in a human subject. In some embodiments, the kit is for identification of bladder cancer according to the method of the present invention. In some embodiments, the kit comprises at least one methylation-sensitive restriction enzyme; pairs of primers for amplification of at least one restriction locus and at least one control locus; means for detecting amplification products of the at least one restriction locus and at least one control locus; and instruction manual for carrying out the identification of bladder cancer. In some embodiments, the instruction manual may be an electronic instruction manual.

In some embodiments, the instruction manual may provide bladder cancer reference ratios and optionally healthy reference ratios.

In some embodiments, the instruction manual may include instructions for performing the method steps described above.

In some embodiments, the instruction manual may include instructions directing the correlation between signal ratio(s) and bladder cancer reference ratio(s) and optionally with healthy reference ratio(s).

In some embodiments, the instruction manual may provide instructions for calculating a marker score, i.e., a score for a given restriction locus. In some embodiments, the instruction manual may provide instructions for calculating a total score for a plurality of marker scores. In some embodiments, the instruction manual may provide a threshold score for determining bladder cancer, above which a subject is identified as having cancer. In other embodiments, the instruction manual may provide a threshold score for determining bladder cancer, below which a subject is identified as having cancer.

In some embodiments, the kit comprises a single methylation-sensitive endonuclease. In some embodiments, the methylation-sensitive endonuclease is HhaI.

In some embodiments, the kit may further comprise a computer software. In some embodiments, the computer software may be a computer software that calculates at least one of signal intensities, signal ratios and marker scores.

In some embodiments, the kit comprises: HhaI; primer pairs complementary to at least one restriction locus and at least one control locus as described herein; and fluorescent polynucleotide probes complementary to the at least one restriction locus and at least one control locus.

Exemplary primers for amplifying the restriction loci set forth in SEQ ID NOs: 1-15 are set forth in SEQ ID NOs: 25-155 as follows (for=forward, rev=reverse):

Locus 1 for.: SEQ ID NOs: 25-29; Locus 1 rev.: SEQ ID NOs: 30-35

Locus 2 for.: SEQ ID NOs: 36-38; Locus 2 rev.: SEQ ID NOs: 39-42

Locus 3 for.: SEQ ID NOs: 43-51; Locus 3 rev.: SEQ ID NOs: 52-61

Locus 4 for.: SEQ ID NOs: 62-64; Locus 4 rev.: SEQ ID NOs: 65-67

Locus 5 for.: SEQ ID NOs: 68-70; Locus 5 rev.: SEQ ID NOs: 71-73

Locus 6 for.: SEQ ID NOs: 74-76; Locus 6 rev.: SEQ ID NOs: 77-79

Locus 7 for.: SEQ ID NOs: 80-85; Locus 7 rev.: SEQ ID NOs: 86-89

Locus 8 for.: SEQ ID NOs: 90-92; Locus 8 rev.: SEQ ID NOs: 93-95

Locus 9 for.: SEQ ID NOs: 96-99; Locus 9 rev.: SEQ ID NOs: 100-102

Locus 10 for.: SEQ ID NOs: 103-106; Locus 10 rev.: SEQ ID NOs: 107-112

Locus 11 for.: SEQ ID NOs: 113-116; Locus 11 rev.: SEQ ID NOs: 117-120

Locus 12 for.: SEQ ID NOs: 121-125; Locus 12 rev.: SEQ ID NOs: 126-130

Locus 13 for.: SEQ ID NOs: 131-135; Locus 13 rev.: SEQ ID NOs: 136-140

Locus 14 for.: SEQ ID NOs: 141-145; Locus 14 rev.: SEQ ID NOs: 146-151

Locus 15 for.: SEQ ID NOs: 152-153; Locus 15 rev.: SEQ ID NOs: 154-155.

Exemplary primers for amplifying the control locus set forth in SEQ ID NO: 16 are set forth in SEQ ID NOs: 156-167 as follows:

Control for.: SEQ ID NOs: 156-161;

Control rev.: SEQ ID NOs: 162-167.

In some embodiments, the kit comprises at least one of a first control construct and a second control construct, each comprising non-human/artificial DNA sequences as described above. In some embodiments, the kit comprises both first and second control constructs as described above.

In some embodiments, the kit comprises one or more containers filled with at least one nucleotide primer pair. In some embodiments, each nucleotide primer pair included in the kit of the present invention may include primers that are complementary to sub-sequences within a restriction locus selected from the restriction loci set forth in SEQ ID NOs: 1-15 or to flanking sequences thereof, wherein said each nucleotide primer pair is designed to selectively amplify a fragment of the genome that includes the locus.

In some embodiments, the kit may comprise primer pairs for selectively amplifying the combination of loci described above.

In some embodiments, the kit may further comprise nucleotide primer pairs for selectively amplifying the first and second artificial control constructs.

In some embodiments, the kit may further include oligonucleotide probes for detecting amplification products of the loci amplified using the primers in the kit. Each oligonucleotide probe may be complementary to a sub-sequence within a locus and may be capable of hybridizing thereto. In some embodiments, the oligonucleotide probes may be fluorescently-labeled.

In some embodiments, the kit may further include at least one additional ingredient needed for DNA digestion, loci amplification and detection of amplification products, such as DNA polymerase and nucleotide mix.

In some embodiments, the kit may further include suitable reaction buffers for digestion and amplification, and a written protocol for performing bladder cancer identification. The written protocol may comprise instructions for performing any of the steps disclosed herein, including but not limited to, DNA digestion parameters, PCR cycling parameters, signal ratio analysis, and comparison to reference ratios.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1

Genomic Loci for Detection of Bladder Cancer

Fifteen (15) human genomic loci were identified as having increased methylation in bladder cancer tissue compared to normal tissue (Table 1 herein below, SEQ ID NOs: 1-15). These loci were found to enable distinguishing between DNA from bladder cancer patients and that of normal individuals (not afflicted with bladder cancer).

TABLE 1

| | Genomic loci | |
|---|---|---|
| SEQ ID NO | Nucleic acid sequence | Description* |
| 1 | TTTTTAGGGGTCTGCGCGCTCTCGCC TGGCTGCTGGGAAGGAGGGCTGGGA GGCGCTGAA | Position 65676359-65676418 on Chromosome 17, KCNJ2 gene |
| 2 | TCCAGGCGCGCCGACCGCTCAAGCG CTCCAGGTCCACCCGGCGGAGGGCA GAGAAAGCGCGACCGCGCGGCCCG CAGGGTTGCAAGAAGAAAACGAGT GTTATATAATGAGTCTCAGTGGTTG CTCACAA TGCCAGGCGC | Position 21958446-21958585 on Chromosome 9, CDKN2A gene |
| 3 | GGCTGATACCAGAGAGGACCCGGA GCGCGAACCAGAGGTTCGACCTCCA G GGCAGCGCAG | Position 336844-336903 on Chromosome 6, IRF4 gene |
| 4 | GGGGCGCCAAATGCCCACGTGTTGA TGAAACCAGTGAGATGGGAACAGG CGGCGGGAAACCAGACAGAGGAAG AGCTAGGGAGGAGACCCCAGCCCCG GATCCTGGGTCGCCAGGGTTTTCCG CGCGCAT | Position 33319507-33319636 on Chromosome 21, Olig2 gene |
| 5 | TCTGAGAAGTGTCCTCCTCGCTCTCT TATAAAAACAGGACTTGTTGCCGAG GTCAGCGCG CGCATCGAGT | Position 166502151-166502220 on Chromosome 6, intergenic region |
| 6 | ATCAGCGCGAACTATTCGTTTAGTG GCCTTAAAACACCCTGGTTTCACCCT CAGCTATTTTCAAGTTCCCGTGTGCC TGGCACTTTCTCCGTGCGAGAAGCA CCGGAGGGTGCGGACGCGCCACAGT CTG | Position 896902-897031 on Chromosome 18, ADCYAP1 gene |
| 7 | TGCTCTGCGCAGCGTGGAGGGCAAC GGGACTGGGAGGCGGCTTCTGCCGC CGGGCACTCGCTTCCAGGTGGCTTA CGAGGATTCAGACTGTGGGAACCGT GCGCTCTTCAGCTTGGTGGACCGCG TGGCGGCGGCGCGGGGCGCCAAGCC | Position 32747873-32748022 on Chromosome 5, NPR3 gene |
| 8 | CGCGCAGAACTTTGCGGTGGCGCTT AGCGCCTCCTTTGCCCAGACCCTTCC CGCCTTTGCCGCGCCCAGA | Position 27949195-27949264 on Chromosome 6, intergenic region |
| 9 | CGTAATCGCCGGTGTAACTCATGTT GGCTGGGGGCCTCCCGGCGCGCGC GGAGAGGCTG GGGTGCGCCC | Position 27191603-27191672 on Chromosome 7, HOXA9 gene |
| 10 | CGATTCAGAGGGCCCCGGTCGGAGC TGTCGGAGATTGAGCGCGCGCGGTC CCGGGATCTC | Position 170170302-170170361 on Chromosome 16, intergenic region |
| 11 | CGCGCGGCAGCCCTCCGTGCGCGCA GGCTCGGGTGCGTTGTTCGCGGGGG TGAATTGTGAAGAACCATCGCGGGG TCCTTCCTGCTGAGGCCGCGGACAC CGTGACCTCGCTGCTCTGGGTCTGC AGGGAAACGTAGGAA | Position 30797737-30797876 on Chromosome 15, intergenic region |
| 12 | TGACCTTTAGGGGCTGTTACTCTCAG ACCAGGCCCAGCAGCACCCGGCGCA TTTACGTCGGATCTGACCCCTGCAA GCACCGGCGCGACCGCGCTAGCGG | Position 7936767-7936866 on Chromosome 1, intergenic region |
| 13 | AGAACTTCGTGGGCAGGTAAGCGCG CAGGGCGCGGAGTAAGGATGCGGC AGTGGGGCGACCCCGCTGCGG | Position 170077565-170077634 on Chromosome 1, DNM3 gene: |
| 14 | CTGCCTGCGCTCACTACGGGTTTTTT AGTTGGCGCCTTAATGTTTGTAACA CTTTTAGAGCGCTTGCTCT | Position 1727592-1727661 on Chromosome 2, PXDN gene |
| 15 | GGCCGGGAAGCGCGGGGTGAGAAA GCGAGGTGGGTGGCGAGAGCGTGA GCGCCCCTCTGCTGACCCCGGGGAG CGTGGACTACGAGTTGGCGCCCAAG TCCAGAATCCGCGCGCACCGCGGTA AGCTGCGCCTTTTGAAA | Position 72919092-72919231 on Chromosome 8, MSC gene |
| 16 | AGACTAACTTTTCTCTTGTACAGAAT CATCAGGCTAAATTTTTGGCATTATT TCAGTCCT | Position 121380854-121380913 on Chromosome 7, intergenic region |

*The description refers to position on hg18 genomic build

Example 2

Testing the Panel of Genomic Loci

Urine samples were obtained from 69 bladder cancer patients and 40 healthy subjects, not afflicted with bladder cancer. The bladder cancer patient population comprised of 55 males and 14 females, ages ranging from 41-92 (mean 72). All 69 cancers were TCC (transitional cell carcinoma) with stages distributed: Ta—42 patients, T1—10 patients, T2—10 patients, CIS (Carcinoma in Situ)—8 patients. The healthy population comprised of 33 males and 7 females, ages ranging from 55-88 (mean 70). DNA was extracted from all urine samples using the QIAamp blood mini kit (QIAGEN, Hilden, Germany)

The extracted DNA from each sample was subjected to digestion with the methylation-sensitive restriction endonuclease HhaI. The digestion reaction (total volume 120 microliter) included all of the extracted DNA (not quantified) and HhaI in a digestion buffer. The digestion was carried out at 37° C. for 2 hours.

Next, quantitative Real-Time (RT) PCR was carried out on the digested DNA samples to amplify in each DNA sample the 15 restriction loci detailed in Table 1 above and a control locus as set forth in SEQ ID NO: 16 (see Table 1). The control locus is a locus that does not contain a recognition sequence of HhaI and remains intact when a DNA sample is digested with HhaI regardless of its methylation status. This control locus, also termed an internal reference locus, has an amplification pattern which following digestion with HhaI is not affected by methylation.

In particular, each digested DNA sample was divided into eight (8) aliquots containing 10 microliters of the digested DNA. Seven aliquots were supplemented with primer pairs for amplification of two restriction loci out of the fifteen and the control locus (the control locus is to be amplified in every aliquot). The eighth aliquot was supplemented with a primer pair for amplification of one remaining restriction locus and the control locus. Amplicons of between 75 to 225 bases were amplified, each containing one of the 16 loci along with 5' and 3' flanking sequences of 5-80 bases.

Each amplification reaction (total volume 25 microliter) further contained dNTPs and a reaction buffer. To enable detection of amplification products during amplification, fluorescently-labeled polynucleotide probes (one for each locus) were added to the reaction. The following fluorescent labels were used: FAM, JOE, ROX, and CY5. RT-PCR reactions were carried out in an ABI 7500 FastDx instrument with the following PCR program: initial activation of the enzyme of 95° C. for 10 minutes followed by 45 cycles of 15 seconds at 95° C. followed by 1 minute at 60° C.

Following RT-PCR, quantitative PCR plots showing the change of fluorescent signals from the probes as a function of cycle number were analyzed to calculate the quantification cycle (Cq) for each locus.

FIG. 1 shows exemplary quantitative PCR plots of the control locus and two restriction loci in a sample from a cancer patient (left) and a healthy sample (right). In the sample from a cancer patient, in which the restriction loci have high methylation levels and therefore remained mostly intact when digested with HhaI, the two restriction loci were amplified with high efficiency, i.e. they rose roughly one cycle later than the control locus (which was not cut at all). In the healthy sample, in which the restriction loci are characterized with low methylation levels and were therefore cut extensively when digested with HhaI, the efficiency of amplification was much lower than the efficiency of amplification of the control locus. As can be taken from the figure, the Cq values of the restriction loci differ between cancer patients and healthy subject.

For each sample, ratios were calculated between the signal intensity of each of restriction loci 1-15 (SEQ ID NO: 1-15) and the signal intensity of the control locus (SEQ ID NO: 16), as follows: the Cq was determined for each restriction locus and for the control locus. The Cq values were used in the following formula:

$$2^{(Cq\ of\ control\ locus - Cq\ of\ restriction\ locus)}$$

It is to be understood that the calculation was performed for a restriction locus and a control locus that were co-amplified in the same aliquot.

The numerical value obtained for each restriction locus with respect to the control locus represents the signal ratio between this restriction locus and the control locus.

Altogether, fifteen ratios (i.e., fifteen calculations according to the above formula) were calculated for each sample. Table 2 summarizes the mean ratios and standard deviation (Std) of each locus with respect to the control locus in the cancer group and in the control group. As can be seen from the table, the ratios obtained for DNA extracted from samples of bladder cancer are significantly different from the ratios obtained for DNA extracted from samples of healthy (no bladder cancer) volunteers. Specifically, significantly higher ratios (at least one order of magnitude higher) were observed for each locus in the cancer group compared to the control group, highlighting the advantage in using these loci for differentiating between urine samples of bladder cancer patients and those of normal/healthy individuals.

TABLE 2

| | signal ratios | | | |
|---|---|---|---|---|
| Locus (SEQ ID NO) | Cancer | | Control | |
| | Mean ratio | Std | Mean ratio | Std |
| 1 | 0.13980 | 0.30183 | 0.00534 | 0.01060 |
| 2 | 0.01190 | 0.02754 | 0.00090 | 0.00182 |
| 3 | 0.01599 | 0.02506 | 0.00270 | 0.00152 |
| 4 | 0.01760 | 0.02701 | 0.00244 | 0.00352 |
| 5 | 0.06652 | 0.11102 | 0.00529 | 0.01228 |
| 6 | 0.02459 | 0.04334 | 0.00263 | 0.00291 |
| 7 | 0.03484 | 0.05963 | 0.00182 | 0.00733 |
| 8 | 0.03583 | 0.09940 | 0.00262 | 0.00439 |
| 9 | 0.05781 | 0.10562 | 0.00505 | 0.00612 |
| 10 | 0.02006 | 0.03538 | 0.00416 | 0.00294 |
| 11 | 0.00992 | 0.02105 | 0.00041 | 0.00062 |
| 12 | 0.00324 | 0.00770 | 0.00019 | 0.00023 |
| 13 | 0.03143 | 0.05330 | 0.00214 | 0.00204 |
| 14 | 0.05309 | 0.08935 | 0.00107 | 0.00270 |
| 15 | 0.02872 | 0.05965 | 0.00087 | 0.00172 |

Next, sensitivity, specificity and area under an ROC curve (AUC) with respect to identification of bladder cancer were calculated for the locus set forth in SEQ ID NO: 1 and for several combinations, or subsets, of loci. The data is summarized in Table 3.

TABLE 3

| Sensitivity specificity and AUC | | | |
|---|---|---|---|
| Loci (SEQ ID NO) | Sensitivity | Specificity | AUC |
| 1 | 75% | 67% | 0.81 |
| 1 + 5 | 79% | 70% | 0.82 |
| 1 + 5 + 7 + 11 | 82% | 74% | 0.85 |

TABLE 3-continued

Sensitivity specificity and AUC

| Loci (SEQ ID NO) | Sensitivity | Specificity | AUC |
|---|---|---|---|
| 1 + 5 + 7 + 11 + 12 | 85% | 75% | 0.89 |
| 1 + 5 + 7 + 11 + 13 | 84% | 76% | 0.89 |
| 1 + 5 + 7 + 11 + 14 | 85% | 76% | 0.90 |
| All (1-15) | 94% | 84% | 0.93 |

Example 3

Identification of Bladder Cancer Using a Single Restriction Locus

Figure 2:
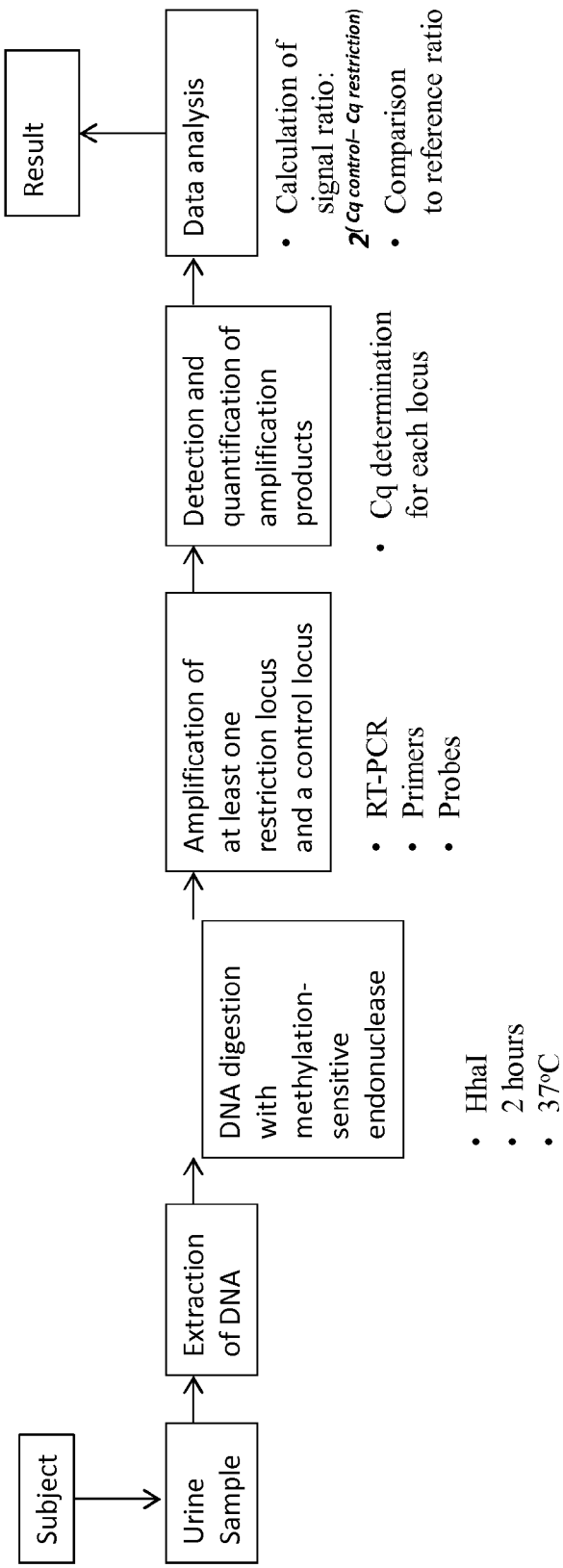
FIG. 2 is a flow-chart describing a method for identifying bladder cancer in a subject according to some embodiments of the present invention.

A urine sample obtained from a subject is analyzed in order to determine the presence of bladder cancer. An exemplary flow chart of the process is shown in FIG. 2. The urine sample is processed as described in Example 2. In particular, DNA is extracted from the sample and subjected to digestion with HhaI. Next, quantitative RT-PCR is carried out to amplify the locus set forth in SEQ ID NO: 1 and the control locus set forth in SEQ ID NO: 16. The digested DNA sample is mixed in a reaction buffer with Taq Polymerase, two pairs of forward and reverse primers (a pair for each locus), dNTPs and two fluorescently-labeled polynucleotide probes (FAM and ROX) to enable detection and quantification of amplification products. RT-PCR reactions are carried-out as described above.

Quantitative PCR plots are analyzed to calculate the quantification cycle (Cq) for each locus. Next, a ratio is calculated between the signal intensity of the locus set forth in SEQ ID NO: 1 and the control locus. In particular, the following calculation is performed:

$$2^{(Cq\ SEQ\ ID\ NO:\ 16 - Cq\ SEQ\ ID\ NO:\ 1)}.$$

The ratio calculated for the tested sample is compared against the distribution of ratios calculated for SEQ ID NO: 16 and SEQ ID NO: 1 in the 109 reference samples analyzed in Example 2 above (69 cancer patients and 40 healthy individuals). Lower ratios generally represent healthy individuals while higher ratios generally represent bladder cancer patients. The calculated ratio is given a score based on its relative position within the distribution. A threshold score is defined, differentiating bladder cancer patients from individuals with no bladder cancer. Detecting a score above the predefined threshold identifies the subject as having bladder cancer. Conversely, detecting a score below the predefined threshold identifies the subject as not having bladder cancer.

Example 4

Identification of Bladder Cancer Using a Combination of Restriction Loci

A urine sample obtained from a subject is analyzed in order to determine the presence of bladder cancer. The urine sample is processed to extract DNA, and the extracted DNA is subjected to digestion with HhaI. Next, quantitative RT-PCR is carried out to amplify a combination of restriction loci and the control locus set forth in SEQ ID NO: 16.

Combination of Four Restriction Loci

The four restriction loci set forth in SEQ ID NOs: 1, 5, 7 and 11 are amplified in addition to the control locus. The digested DNA is mixed with five primer pairs (one for each restriction locus and a pair for the control locus) and five polynucleotide probes among other components needed for amplification. The mixture is subjected to RT-PCR.

Quantitative PCR plots are analyzed to calculate the quantification cycle (Cq) for each locus. Next, ratios are calculated between the signal intensity of each of the restriction loci set forth in SEQ ID NOs: 1, 5, 7 and 11, and the control locus, a total of four ratios. In particular, the following calculation is performed for each restriction locus:
$2^{(Cq\ SEQ\ ID\ NO:\ 16 - Cq\ restriction\ locus)}$.

Combination of Fifteen Restriction Loci

Fifteen (15) restriction loci (SEQ ID NOs: 1-15) are amplified in addition to the control locus. The digested DNA sample is divided into eight (8) aliquots, seven of which are supplemented with primer pairs for amplification of two restriction loci out of the fifteen and the control locus. The eighth aliquot is supplemented with primer pairs for amplification of one remaining restriction locus and the control locus. Each aliquot is further supplemented with the appropriate polynucleotide probes (two or three probes, depending on the number of loci to be amplified and detected) and other components needed for amplification. All aliquots are subjected to RT-PCR.

For each aliquot, a quantitative PCR plot is obtained, showing data for the control locus and one or two restriction loci. Each plot is analyzed to calculate the quantification cycle (Cq) for each locus. Next, ratios are calculated between the signal intensity of each of the restriction loci set forth in SEQ ID NOs: 1-15 and the control locus, a total of fifteen ratios. In particular, the following calculation is performed for each restriction locus:
$2^{(Cq\ SEQ\ ID\ NO:\ 16 - Cq\ restriction\ locus)}$.

Data Analysis

Each of the obtained ratios (for each locus) is compared against the distribution of ratios calculated for this locus in the 109 healthy and cancer reference samples and a score is given to each locus based on its relative position within the distribution, as described above. The individual scores calculated for each ratio (for each locus) are combined to give a single score. The single score is used for determining whether the subject is having cancer, where a score above a pre-defined threshold is indicative of bladder cancer.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

What is claimed is:

1. A method for measuring methylation ratio of DNA in a human subject suspected of having bladder cancer, the method comprising:
   (a) obtaining a sample of DNA from a urine sample of the subject, and subjecting the DNA sample to digestion with at least one methylation-sensitive restriction endonuclease to obtain restriction endonuclease-treated DNA;
   (b) co-amplifying from the restriction endonuclease-treated DNA at least one restriction locus comprising the locus set forth in SEQ ID NO: 1 and a control locus, thereby generating an amplification product for each locus and generating data from the amplification product that identifies the methylation ratio of the DNA sample of the human subject.

2. The method of claim 1, wherein the at least one restriction locus further comprises the locus set forth in SEQ ID NO: 5.

3. The method of claim 2, wherein the at least one restriction locus further comprises the locus set forth in SEQ ID NO: 7 and the locus set forth in SEQ ID NO: 11.

4. The method of claim 3, wherein the at least one restriction locus further comprises at least one additional restriction locus selected from the group of loci set forth in SEQ ID NO: 2, SEQ ID NO: 3, SEQ ID NO: 4, SEQ ID NO: 6, SEQ ID NO: 8, SEQ ID NO: 9, SEQ ID NO: 10, SEQ ID NO: 12, SEQ ID NO: 13, SEQ ID NO: 14 and SEQ ID NO: 15.

5. The method of claim 4, wherein the at least one additional restriction locus comprises the loci set forth in SEQ ID NO: 2, SEQ ID NO: 3, SEQ ID NO: 4, SEQ ID NO: 6, SEQ ID NO: 8, SEQ ID NO: 9, SEQ ID NO: 10, SEQ ID NO: 12, SEQ ID NO: 13, SEQ ID NO: 14 and SEQ ID NO: 15.

6. The method of claim 1, further comprising:
   providing a first and second control constructs comprising non-human DNA sequences, wherein the first control construct comprises a DNA sequence devoid of a recognition sequence of the methylation-sensitive restriction endonuclease, and the second control construct comprises a DNA sequence containing a recognition sequence of the methylation-sensitive restriction endonuclease and being completely unmethylated;
   digesting the first and second control constructs with the methylation-sensitive restriction endonuclease; and
   amplifying the first and second control constructs;
   wherein detection of adequate amplification for the first construct concomitant with low or absence of amplification for the second construct is indicative of proper DNA digestion.

7. The method of claim 1, wherein the at least one methylation-sensitive restriction endonuclease is selected from the group consisting of AatII, Acc65I, AccI, AciI, AclI, AfeI, AgeI, ApaI, ApaLI, AscI, AsiSI, AvaI, AvaII, BaeI, BanI, BbeI, BceAI, BcgI, BfuCI, BglI, BmgBI, BsaAI, BsaBI, BsaHI, BsaI, BseYI, BsiEI, BsiWI, BslI, BsmAI, BsmBI, BsmFI, BspDI, BsrBI, BsrFI, BssHII, BssKI, BstAPI, BstBI, BstUI, BstZ17I, Cac8I, ClaI, DpnI, DrdI, EaeI, EagI, EagI-HF, EciI, EcoRI, EcoRI-HF, FauI, Fnu4HI, FseI, FspI, HaeII, HgaI, HhaI, HincII, HincII, HinfI, HinP1I, HpaI, HpaII, Hpy166ii, Hpy188iii, Hpy99I, HpyCH4IV, KasI, MluI, MmeI, MspA1I, MwoI, NaeI, NacI, NgoNIV, Nhe-HFI, NheI, NlaIV, NotI, NotI-HF, NruI, Nt.BbvCI, Nt.BsmAI, Nt.CviPII, PaeR7I, PleI, PmeI, PmlI, PshAI, PspOMI, PvuI, RsaI, RsrII, SacII, SalI, SalI-HF, Sau3AI, Sau96I, ScrFI, SfiI, SfoI, SgrAI, SmaI, SnaBI, TfiI, TscI, TseI, TspMI, and ZraI.

8. The method of claim 1, wherein step (a) is performed using one methylation-sensitive restriction endonuclease.

9. The method of claim 8, wherein the methylation-sensitive restriction endonuclease is HhaI.

10. The method of claim 1, wherein the control locus is a locus devoid of a recognition sequence of the methylation-sensitive restriction endonuclease.

11. The method of claim 10, wherein the control locus is the locus set forth in SEQ ID NO: 16.

12. The method of claim 1, wherein step (b) is performed using real-time PCR.

13. The method of claim 12, wherein the method further comprises adding fluorescent probes for specifically detecting the amplification products of the at least one restriction locus and the control locus.

14. The method of claim 12, wherein said methylation ratio is between a signal intensity of the amplification products of said at least one restriction locus and a signal intensity of the amplification product of the control locus which is calculated by calculating $2^{(C_q\ control\ locus - C_q\ restriction\ locus)}$, wherein $C_q$ is a quantification cycle.

15. The method of claim 1, further comprising providing a healthy reference ratio between a signal intensity of the amplification products of the at least one restriction locus and a signal intensity of the control locus in DNA derived from healthy subjects.

16. The method of claim 1, wherein said bladder cancer is selected from the group consisting of transitional cell carcinoma, squamous cell carcinoma, adenocarcinoma, sarcoma and small cell carcinoma.

17. The method of claim 1, wherein said bladder cancer is transitional cell carcinoma.

18. A method of treating bladder cancer in a subject in need thereof comprising identifying the methylation status of the subject's DNA which is measured according to the method of claim 1, and administering to said subject anti-bladder cancer therapy.

19. The method of claim 18, wherein said anti-bladder cancer therapy comprises one or more of: surgery, radiation therapy, chemotherapy or immunotherapy.

20. A method for measuring methylation status of DNA in a human subject suspected of having bladder cancer, the method comprising:
   (a) obtaining a sample of DNA from a urine sample of the subject, and subjecting the DNA sample to digestion with at least one methylation-sensitive restriction endonuclease to obtain restriction endonuclease-treated DNA;
   (b) co-amplifying from the restriction endonuclease-treated DNA at least one restriction locus comprising the locus set forth in SEQ ID NO: 1 and a control locus, thereby generating an amplification product for each locus, and
   (c) generating data from the amplification product that identifies the methylation status of the DNA sample of the human subject.

21. A method of treating bladder cancer in a subject in need thereof comprising the methylation status of the subject's DNA which is measured according to the method of claim 1, and administering to said subject anti-bladder cancer therapy.

22. The method of claim 21, wherein said anti-bladder cancer therapy comprises one or more of: surgery, radiation therapy, chemotherapy or immunotherapy.

* * * * *

SEQUENCE LISTING

<160> NUMBER OF SEQ ID NOS: 167

<210> SEQ ID NO 1
<211> LENGTH: 60
<212> TYPE: DNA
<213> ORGANISM: Homo sapiens

<400> SEQUENCE: 1
tttttagggg tctgcgcgct ctcgcctggc tgctgggaag gagggctggg aggcgctgaa    60

<210> SEQ ID NO 2
<211> LENGTH: 140
<212> TYPE: DNA
<213> ORGANISM: Homo sapiens

<400> SEQUENCE: 2
tccaggcgcg ccgaccgctc aagcgctcca ggtccacccg gcggagggca gagaaagcgc    60
gaccgcgcgg cccgcagggt tgcaagaaga aaacgagtgt tatataatga gtctcagtgg   120
ttgctcacaa tgccaggcgc                                                140

<210> SEQ ID NO 3
<211> LENGTH: 60
<212> TYPE: DNA
<213> ORGANISM: Homo sapiens

<400> SEQUENCE: 3
ggctgatacc agagaggacc cggagcgcga accagaggtt cgacctccag ggcagcgcag    60

<210> SEQ ID NO 4
<211> LENGTH: 130
<212> TYPE: DNA
<213> ORGANISM: Homo sapiens

<400> SEQUENCE: 4
ggggcgccaa atgcccacgt gttgatgaaa ccagtgagat gggaacaggc ggcgggaaac    60
cagacagagg aagagctagg gaggagaccc cagccccgga tcctgggtcg ccagggtttt   120
ccgcgcgcat                                                           130

<210> SEQ ID NO 5
<211> LENGTH: 70
<212> TYPE: DNA
<213> ORGANISM: Homo sapiens

<400> SEQUENCE: 5
tctgagaagt gtcctcctcg ctctcttata aaaacaggac ttgttgccga ggtcagcgcg    60
cgcatcgagt                                                           70

<210> SEQ ID NO 6
<211> LENGTH: 130
<212> TYPE: DNA
<213> ORGANISM: Homo sapiens

<400> SEQUENCE: 6
atcagcgcga actattcgtt tagtggcctt aaaacaccct ggtttcaccc tcagctattt    60
tcaagttccc gtgtgcctgg cactttctcc gtgcgagaag caccggaggg tgcggacgcg   120
ccacagtctg                                                           130

<210> SEQ ID NO 7
<211> LENGTH: 150

<212> TYPE: DNA
<213> ORGANISM: Homo sapiens

<400> SEQUENCE: 7

```
tgctctgcgc agcgtggagg gcaacgggac tgggaggcgg cttctgccgc cgggcactcg    60
cttccaggtg gcttacgagg attcagactg tgggaaccgt gcgctcttca gcttggtgga   120
ccgcgtggcg gcggcgcggg gcgccaagcc                                    150
```

<210> SEQ ID NO 8
<211> LENGTH: 70
<212> TYPE: DNA
<213> ORGANISM: Homo sapiens

<400> SEQUENCE: 8

```
cgcgcagaac tttgcggtgg cgcttagcgc ctcctttgcc cagacccttc ccgcctttgc    60
cgcgcccaga                                                          70
```

<210> SEQ ID NO 9
<211> LENGTH: 70
<212> TYPE: DNA
<213> ORGANISM: Homo sapiens

<400> SEQUENCE: 9

```
cgtaatcgcc ggtgtaactc atgttggctg gggggcctcc cggcgcgcgc ggagaggctg    60
gggtgcgccc                                                          70
```

<210> SEQ ID NO 10
<211> LENGTH: 60
<212> TYPE: DNA
<213> ORGANISM: Homo sapiens

<400> SEQUENCE: 10

```
cgattcagag ggccccggtc ggagctgtcg gagattgagc gcgcgcggtc ccgggatctc    60
```

<210> SEQ ID NO 11
<211> LENGTH: 140
<212> TYPE: DNA
<213> ORGANISM: Homo sapiens

<400> SEQUENCE: 11

```
cgcgcggcag ccctccgtgc gcgcaggctc gggtgcgttg ttcgcggggg tgaattgtga    60
agaaccatcg cggggtcctt cctgctgagg ccgcggacac cgtgacctcg ctgctctggg   120
tctgcaggga aacgtaggaa                                               140
```

<210> SEQ ID NO 12
<211> LENGTH: 100
<212> TYPE: DNA
<213> ORGANISM: Homo sapiens

<400> SEQUENCE: 12

```
tgacctttag gggctgttac tctcagacca ggcccagcag cacccggcgc atttacgtcg    60
gatctgaccc ctgcaagcac cggcgcgacc gcgctagcgg                         100
```

<210> SEQ ID NO 13
<211> LENGTH: 70
<212> TYPE: DNA
<213> ORGANISM: Homo sapiens

<400> SEQUENCE: 13
```

```
agaacttcgt gggcaggtaa gcgcgcaggg cgcggagtaa ggatgcggca gtggggcgac    60
cccgctgcgg                                                          70
```

<210> SEQ ID NO 14
<211> LENGTH: 70
<212> TYPE: DNA
<213> ORGANISM: Homo sapiens

<400> SEQUENCE: 14

```
ctgcctgcgc tcactacggg ttttttagtt ggcgccttaa tgtttgtaac acttttagag    60
cgcttgctct                                                          70
```

<210> SEQ ID NO 15
<211> LENGTH: 140
<212> TYPE: DNA
<213> ORGANISM: Homo sapiens

<400> SEQUENCE: 15

```
ggccgggaag cgcggggtga aaagcgagg tgggtggcga gagcgtgagc gcccctctgc     60
tgacccCggg gagcgtggac tacgagttgg cgcccaagtc cagaatccgc gcgcaccgcg   120
gtaagctgcg ccttttgaaa                                               140
```

<210> SEQ ID NO 16
<211> LENGTH: 60
<212> TYPE: DNA
<213> ORGANISM: Homo sapiens

<400> SEQUENCE: 16

```
agactaactt ttctcttgta cagaatcatc aggctaaatt tttggcatta tttcagtcct    60
```

<210> SEQ ID NO 17
<211> LENGTH: 80
<212> TYPE: DNA
<213> ORGANISM: Artificial Sequence
<220> FEATURE:
<223> OTHER INFORMATION: Control construct

<400> SEQUENCE: 17

```
aagtctcgag tcgatgtcac taaccatgag tattccatgt gccgtcatct aacaagtact    60
gcatacCctg gataatggct                                               80
```

<210> SEQ ID NO 18
<211> LENGTH: 100
<212> TYPE: DNA
<213> ORGANISM: Artificial Sequence
<220> FEATURE:
<223> OTHER INFORMATION: Control construct

<400> SEQUENCE: 18

```
taccaggtct acaaagctcg actctgcctg cgctcactac gggttttta gttggcgcct     60 taatgtttgt aacactttta gagcgcttgc tctgatcctc                         100
```

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19

```
aagtctcgag tcgatgtcac                                               20
```

```
<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
agccattatc cagggtatgc                                              20

<210> SEQ ID NO 21
<211> LENGTH: 23
<212> TYPE: DNA
<213> ORGANISM: Artificial Sequence
<220> FEATURE:
<223> OTHER INFORMATION: Probe

<400> SEQUENCE: 21
accatgagta ttccatgtgc cgt                                          23

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
taccaggtct acaaagctcg ac                                           22

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
acgcctacta atacacatcg gag                                          23

<210> SEQ ID NO 24
<211> LENGTH: 25
<212> TYPE: DNA
<213> ORGANISM: Artificial Sequence
<220> FEATURE:
<223> OTHER INFORMATION: Probe

<400> SEQUENCE: 24
cgctcactac gggttttta gttgg                                         25

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
cagacccggt taacactgaa g                                            21

<210> SEQ ID NO 26
<211> LENGTH: 23
<212> TYPE: DNA
<213> ORGANISM: Artificial Sequence
<220> FEATURE:
```

```
<223> OTHER INFORMATION: Primer

<400> SEQUENCE: 26
gacccggtta acactgaagt tgc                                          23

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ccagacccgg ttaacactga                                              20

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
ccggttaaca ctgaagttgc tt                                           22

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
tccagacccg gttaacactg a                                            21

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
ctcagatctg ccctcgcttc                                              20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
ctcagatctg ccctcgcttc                                              20

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
gcaactccta cagacactca gat                                          23
```

```
<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
gacactcaga tctgccctcg                                              20

<210> SEQ ID NO 34
<211> LENGTH: 25
<212> TYPE: DNA
<213> ORGANISM: Artificial Sequence
<220> FEATURE:
<223> OTHER INFORMATION: Primer

<400> SEQUENCE: 34
atcagaacaa ttagagagta atgat                                        25

<210> SEQ ID NO 35
<211> LENGTH: 19
<212> TYPE: DNA
<213> ORGANISM: Artificial Sequence
<220> FEATURE:
<223> OTHER INFORMATION: Primer

<400> SEQUENCE: 35
cagatctgcc ctcgcttca                                               19

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
ggtccagcag ctagtccact                                              20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
ctccctggtc cagcagctag                                              20

<210> SEQ ID NO 38
<211> LENGTH: 18
<212> TYPE: DNA
<213> ORGANISM: Artificial Sequence
<220> FEATURE:
<223> OTHER INFORMATION: Primer

<400> SEQUENCE: 38
cccgcctggc tgctccag                                                18

<210> SEQ ID NO 39
<211> LENGTH: 21
<212> TYPE: DNA
<213> ORGANISM: Artificial Sequence
<220> FEATURE:
<223> OTHER INFORMATION: Primer
```

-continued

<400> SEQUENCE: 39
caccaggtgc aaaagatgcc t                                              21

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
cgggaaggga aaggccacat                                                20

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
aaggccacat cttcacgcct t                                              21

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
tgagcaacca ctgagactca tt                                             22

<210> SEQ ID NO 43
<211> LENGTH: 19
<212> TYPE: DNA
<213> ORGANISM: Artificial Sequence
<220> FEATURE:
<223> OTHER INFORMATION: Primer

<400> SEQUENCE: 43
cgtcctggag ctccgactc                                                 19

<210> SEQ ID NO 44
<211> LENGTH: 19
<212> TYPE: DNA
<213> ORGANISM: Artificial Sequence
<220> FEATURE:
<223> OTHER INFORMATION: Primer

<400> SEQUENCE: 44
ccgactccca ccccatctg                                                 19

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
ataccagaga ggacccggag                                                20

<210> SEQ ID NO 46
<211> LENGTH: 21

<212> TYPE: DNA
<213> ORGANISM: Artificial Sequence
<220> FEATURE:
<223> OTHER INFORMATION: Primer

<400> SEQUENCE: 46
gaaccagagg ttcgacctcc a                                              21

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47
cccggcttcg gagcgggaa                                                 19

<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
cagtttcacc gctcgatctt g                                              21

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
cgagtccagg gcgaggtaag                                                20

<210> SEQ ID NO 50
<211> LENGTH: 21
<212> TYPE: DNA
<213> ORGANISM: Artificial Sequence
<220> FEATURE:
<223> OTHER INFORMATION: Primer

<400> SEQUENCE: 50
gaggctgata ccagagagga c                                              21

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
cacaactgcc tgcgagaaac a                                              21

<210> SEQ ID NO 52
<211> LENGTH: 19
<212> TYPE: DNA
<213> ORGANISM: Artificial Sequence
<220> FEATURE:
<223> OTHER INFORMATION: Primer

<400> SEQUENCE: 52

```
agcttgtggc gaccccgtc                                              19

<210> SEQ ID NO 53
<211> LENGTH: 21
<212> TYPE: DNA
<213> ORGANISM: Artificial Sequence
<220> FEATURE:
<223> OTHER INFORMATION: Primer

<400> SEQUENCE: 53
tagctcatcc cgtccagctt g                                           21

<210> SEQ ID NO 54
<211> LENGTH: 19
<212> TYPE: DNA
<213> ORGANISM: Artificial Sequence
<220> FEATURE:
<223> OTHER INFORMATION: Primer

<400> SEQUENCE: 54
cgcctcagcc actcctggg                                              19

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
ggccttggag cccaaaccag                                             20

<210> SEQ ID NO 56
<211> LENGTH: 19
<212> TYPE: DNA
<213> ORGANISM: Artificial Sequence
<220> FEATURE:
<223> OTHER INFORMATION: Primer

<400> SEQUENCE: 56
gctcgggcag agccaagga                                              19

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
tcttgtgtgg gtgccttgga                                             20

<210> SEQ ID NO 58
<211> LENGTH: 22
<212> TYPE: DNA
<213> ORGANISM: Artificial Sequence
<220> FEATURE:
<223> OTHER INFORMATION: Primer

<400> SEQUENCE: 58
ctggaggtcg aacctctggt tc                                          22

<210> SEQ ID NO 59
<211> LENGTH: 19
<212> TYPE: DNA
<213> ORGANISM: Artificial Sequence
```

<220> FEATURE:
<223> OTHER INFORMATION: Primer

<400> SEQUENCE: 59
cgctccgaag ccggggtac        19

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
ggtgggagtc ggagctccag        20

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
ggagcgaccc aaatgtggag        20

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
cctgggcatc gtttacattt gg        22

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
gcatcgttta catttggggc        20

<210> SEQ ID NO 64
<211> LENGTH: 21
<212> TYPE: DNA
<213> ORGANISM: Artificial Sequence
<220> FEATURE:
<223> OTHER INFORMATION: Primer

<400> SEQUENCE: 64
gagtagagca ccaagatagt g        21

<210> SEQ ID NO 65
<211> LENGTH: 20
<212> TYPE: DNA
<213> ORGANISM: Artificial Sequence
<220> FEATURE:
<223> OTHER INFORMATION: Primer

<400> SEQUENCE: 65
gcagccgcac cttttgggat        20

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
gggatgggat ggtttggaga                                           20

<210> SEQ ID NO 67
<211> LENGTH: 23
<212> TYPE: DNA
<213> ORGANISM: Artificial Sequence
<220> FEATURE:
<223> OTHER INFORMATION: Primer

<400> SEQUENCE: 67
gagtctaaca aactaacctg atg                                       23

<210> SEQ ID NO 68
<211> LENGTH: 21
<212> TYPE: DNA
<213> ORGANISM: Artificial Sequence
<220> FEATURE:
<223> OTHER INFORMATION: Primer

<400> SEQUENCE: 68
acaggacttg ttgccgaggt c                                         21

<210> SEQ ID NO 69
<211> LENGTH: 23
<212> TYPE: DNA
<213> ORGANISM: Artificial Sequence
<220> FEATURE:
<223> OTHER INFORMATION: Primer

<400> SEQUENCE: 69
atggacggaa ataagcaaaa gca                                       23

<210> SEQ ID NO 70
<211> LENGTH: 22
<212> TYPE: DNA
<213> ORGANISM: Artificial Sequence
<220> FEATURE:
<223> OTHER INFORMATION: Primer

<400> SEQUENCE: 70
gcaaaagcaa aacaacccct tc                                        22

<210> SEQ ID NO 71
<211> LENGTH: 22
<212> TYPE: DNA
<213> ORGANISM: Artificial Sequence
<220> FEATURE:
<223> OTHER INFORMATION: Primer

<400> SEQUENCE: 71
ttccgtgaaa gcaatgacac ag                                        22

<210> SEQ ID NO 72
<211> LENGTH: 22
<212> TYPE: DNA
<213> ORGANISM: Artificial Sequence
<220> FEATURE:
<223> OTHER INFORMATION: Primer

<400> SEQUENCE: 72
aataaaacaa ccgctgccga ca                                          22

<210> SEQ ID NO 73
<211> LENGTH: 21
<212> TYPE: DNA
<213> ORGANISM: Artificial Sequence
<220> FEATURE:
<223> OTHER INFORMATION: Primer

<400> SEQUENCE: 73
caatgacaca gcagaaacca c                                           21

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
gccaggcact cgctggatct                                             20

<210> SEQ ID NO 75
<211> LENGTH: 21
<212> TYPE: DNA
<213> ORGANISM: Artificial Sequence
<220> FEATURE:
<223> OTHER INFORMATION: Primer

<400> SEQUENCE: 75
ccgccatcga taacagatca g                                           21

<210> SEQ ID NO 76
<211> LENGTH: 20
<212> TYPE: DNA
<213> ORGANISM: Artificial Sequence
<220> FEATURE:
<223> OTHER INFORMATION: Primer

<400> SEQUENCE: 76
ggcaccgcca tcgataacag                                             20

<210> SEQ ID NO 77
<211> LENGTH: 21
<212> TYPE: DNA
<213> ORGANISM: Artificial Sequence
<220> FEATURE:
<223> OTHER INFORMATION: Primer

<400> SEQUENCE: 77
cccctaaact tagccagttc g                                           21

<210> SEQ ID NO 78
<211> LENGTH: 24
<212> TYPE: DNA
<213> ORGANISM: Artificial Sequence
<220> FEATURE:
<223> OTHER INFORMATION: Primer

<400> SEQUENCE: 78
tggcaggaac atgaataata aatg                                        24

<210> SEQ ID NO 79

```
<211> LENGTH: 19
<212> TYPE: DNA
<213> ORGANISM: Artificial Sequence
<220> FEATURE:
<223> OTHER INFORMATION: Primer

<400> SEQUENCE: 79
ggcggcggct cagactgtg                                            19

<210> SEQ ID NO 80
<211> LENGTH: 21
<212> TYPE: DNA
<213> ORGANISM: Artificial Sequence
<220> FEATURE:
<223> OTHER INFORMATION: Primer

<400> SEQUENCE: 80
ggcttacgag gattcagact g                                         21

<210> SEQ ID NO 81
<211> LENGTH: 19
<212> TYPE: DNA
<213> ORGANISM: Artificial Sequence
<220> FEATURE:
<223> OTHER INFORMATION: Primer

<400> SEQUENCE: 81
ggactgggag gcggcttct                                            19

<210> SEQ ID NO 82
<211> LENGTH: 19
<212> TYPE: DNA
<213> ORGANISM: Artificial Sequence
<220> FEATURE:
<223> OTHER INFORMATION: Primer

<400> SEQUENCE: 82
cgtggagggc aacgggact                                            19

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
cactcgcttc caggtggctt                                           20

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
cggccatcga gtatgctctg                                           20

<210> SEQ ID NO 85
<211> LENGTH: 23
<212> TYPE: DNA
<213> ORGANISM: Artificial Sequence
<220> FEATURE:
<223> OTHER INFORMATION: Primer

<400> SEQUENCE: 85
```

-continued

```
gatgactcgt acttgttttc act                                          23

<210> SEQ ID NO 86
<211> LENGTH: 21
<212> TYPE: DNA
<213> ORGANISM: Artificial Sequence
<220> FEATURE:
<223> OTHER INFORMATION: Primer

<400> SEQUENCE: 86
cccaggataa ggtctggctt g                                            21

<210> SEQ ID NO 87
<211> LENGTH: 21
<212> TYPE: DNA
<213> ORGANISM: Artificial Sequence
<220> FEATURE:
<223> OTHER INFORMATION: Primer

<400> SEQUENCE: 87
ctgctgcata ctcgcacact g                                            21

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
cacactggcc ccaggataag                                              20

<210> SEQ ID NO 89
<211> LENGTH: 19
<212> TYPE: DNA
<213> ORGANISM: Artificial Sequence
<220> FEATURE:
<223> OTHER INFORMATION: Primer

<400> SEQUENCE: 89
gatgcaagcc gggccactg                                               19

<210> SEQ ID NO 90
<211> LENGTH: 21
<212> TYPE: DNA
<213> ORGANISM: Artificial Sequence
<220> FEATURE:
<223> OTHER INFORMATION: Primer

<400> SEQUENCE: 90
ggtgatgccc tgaatgttgt c                                            21

<210> SEQ ID NO 91
<211> LENGTH: 19
<212> TYPE: DNA
<213> ORGANISM: Artificial Sequence
<220> FEATURE:
<223> OTHER INFORMATION: Primer

<400> SEQUENCE: 91
cttaacgcct ccacgccgt                                               19

<210> SEQ ID NO 92
<211> LENGTH: 18
<212> TYPE: DNA
```

```
<213> ORGANISM: Artificial Sequence
<220> FEATURE:
<223> OTHER INFORMATION: Primer

<400> SEQUENCE: 92
ccgtgccagg cgtcggat                                                   18

<210> SEQ ID NO 93
<211> LENGTH: 24
<212> TYPE: DNA
<213> ORGANISM: Artificial Sequence
<220> FEATURE:
<223> OTHER INFORMATION: Primer

<400> SEQUENCE: 93
tttgtttagt acaagacatg tctg                                            24

<210> SEQ ID NO 94
<211> LENGTH: 23
<212> TYPE: DNA
<213> ORGANISM: Artificial Sequence
<220> FEATURE:
<223> OTHER INFORMATION: Primer

<400> SEQUENCE: 94
cgtgttgcat tttgtttagt aca                                             23

<210> SEQ ID NO 95
<211> LENGTH: 19
<212> TYPE: DNA
<213> ORGANISM: Artificial Sequence
<220> FEATURE:
<223> OTHER INFORMATION: Primer

<400> SEQUENCE: 95
gctgcgaggc ttgccgtgt                                                  19

<210> SEQ ID NO 96
<211> LENGTH: 21
<212> TYPE: DNA
<213> ORGANISM: Artificial Sequence
<220> FEATURE:
<223> OTHER INFORMATION: Primer

<400> SEQUENCE: 96
actcggtgtt ctcaccgaaa g                                               21

<210> SEQ ID NO 97
<211> LENGTH: 21
<212> TYPE: DNA
<213> ORGANISM: Artificial Sequence
<220> FEATURE:
<223> OTHER INFORMATION: Primer

<400> SEQUENCE: 97
acgtaatcgc cggtgtaact c                                               21

<210> SEQ ID NO 98
<211> LENGTH: 22
<212> TYPE: DNA
<213> ORGANISM: Artificial Sequence
<220> FEATURE:
<223> OTHER INFORMATION: Primer

<400> SEQUENCE: 98
cctttctttg tagccacctc ag                                              22
```

```
<210> SEQ ID NO 99
<211> LENGTH: 21
<212> TYPE: DNA
<213> ORGANISM: Artificial Sequence
<220> FEATURE:
<223> OTHER INFORMATION: Primer

<400> SEQUENCE: 99
ggaagcaaca gatcgtcact c                                           21

<210> SEQ ID NO 100
<211> LENGTH: 22
<212> TYPE: DNA
<213> ORGANISM: Artificial Sequence
<220> FEATURE:
<223> OTHER INFORMATION: Primer

<400> SEQUENCE: 100
ttgagcacaa gcatgctgca tg                                          22

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
ccctctgcac actcgagaac                                             20

<210> SEQ ID NO 102
<211> LENGTH: 21
<212> TYPE: DNA
<213> ORGANISM: Artificial Sequence
<220> FEATURE:
<223> OTHER INFORMATION: Primer

<400> SEQUENCE: 102
ggacgagagt tgagctctca c                                           21

<210> SEQ ID NO 103
<211> LENGTH: 21
<212> TYPE: DNA
<213> ORGANISM: Artificial Sequence
<220> FEATURE:
<223> OTHER INFORMATION: Primer

<400> SEQUENCE: 103
aggttgcagt gagccggaat g                                           21

<210> SEQ ID NO 104
<211> LENGTH: 25
<212> TYPE: DNA
<213> ORGANISM: Artificial Sequence
<220> FEATURE:
<223> OTHER INFORMATION: Primer

<400> SEQUENCE: 104
aataccatat agtgaacacc taaga                                       25

<210> SEQ ID NO 105
<211> LENGTH: 24
<212> TYPE: DNA
<213> ORGANISM: Artificial Sequence
<220> FEATURE:
```

<223> OTHER INFORMATION: Primer

<400> SEQUENCE: 105
ccaatttttg tgtttttagt agag                                    24

<210> SEQ ID NO 106
<211> LENGTH: 20
<212> TYPE: DNA
<213> ORGANISM: Artificial Sequence
<220> FEATURE:
<223> OTHER INFORMATION: Primer

<400> SEQUENCE: 106
ggatccaggg cgattcagag                                         20

<210> SEQ ID NO 107
<211> LENGTH: 19
<212> TYPE: DNA
<213> ORGANISM: Artificial Sequence
<220> FEATURE:
<223> OTHER INFORMATION: Primer

<400> SEQUENCE: 107
cagggcctcg tcggagatc                                          19

<210> SEQ ID NO 108
<211> LENGTH: 19
<212> TYPE: DNA
<213> ORGANISM: Artificial Sequence
<220> FEATURE:
<223> OTHER INFORMATION: Primer

<400> SEQUENCE: 108
tcgtcggaga tcccgggac                                          19

<210> SEQ ID NO 109
<211> LENGTH: 21
<212> TYPE: DNA
<213> ORGANISM: Artificial Sequence
<220> FEATURE:
<223> OTHER INFORMATION: Primer

<400> SEQUENCE: 109
tgctgcccag cttcttccac a                                       21

<210> SEQ ID NO 110
<211> LENGTH: 17
<212> TYPE: DNA
<213> ORGANISM: Artificial Sequence
<220> FEATURE:
<223> OTHER INFORMATION: Primer

<400> SEQUENCE: 110
ggtcccgcgg cctccag                                            17

<210> SEQ ID NO 111
<211> LENGTH: 17
<212> TYPE: DNA
<213> ORGANISM: Artificial Sequence
<220> FEATURE:
<223> OTHER INFORMATION: Primer

<400> SEQUENCE: 111
gcagcttcgc cgcccgg                                            17

```
<210> SEQ ID NO 112
<211> LENGTH: 18
<212> TYPE: DNA
<213> ORGANISM: Artificial Sequence
<220> FEATURE:
<223> OTHER INFORMATION: Primer

<400> SEQUENCE: 112
cggaccggcc aggggtcc                                                 18

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
caggacccgc tcagttccac                                               20

<210> SEQ ID NO 114
<211> LENGTH: 19
<212> TYPE: DNA
<213> ORGANISM: Artificial Sequence
<220> FEATURE:
<223> OTHER INFORMATION: Primer

<400> SEQUENCE: 114
cagggatgtg agtgggcgg                                                19

<210> SEQ ID NO 115
<211> LENGTH: 20
<212> TYPE: DNA
<213> ORGANISM: Artificial Sequence
<220> FEATURE:
<223> OTHER INFORMATION: Primer

<400> SEQUENCE: 115
gaagagggcc gcaaaccaac                                               20

<210> SEQ ID NO 116
<211> LENGTH: 19
<212> TYPE: DNA
<213> ORGANISM: Artificial Sequence
<220> FEATURE:
<223> OTHER INFORMATION: Primer

<400> SEQUENCE: 116
acccgccgca ctgacaggt                                                19

<210> SEQ ID NO 117
<211> LENGTH: 22
<212> TYPE: DNA
<213> ORGANISM: Artificial Sequence
<220> FEATURE:
<223> OTHER INFORMATION: Primer

<400> SEQUENCE: 117
tttcctacgt ttccctgcag ac                                            22

<210> SEQ ID NO 118
<211> LENGTH: 20
<212> TYPE: DNA
<213> ORGANISM: Artificial Sequence
<220> FEATURE:
<223> OTHER INFORMATION: Primer
```

-continued

<400> SEQUENCE: 118
atcctgcccg ctcctgacaa                                               20

<210> SEQ ID NO 119
<211> LENGTH: 20
<212> TYPE: DNA
<213> ORGANISM: Artificial Sequence
<220> FEATURE:
<223> OTHER INFORMATION: Primer

<400> SEQUENCE: 119
ccagcaccag gagcgtgttc                                               20

<210> SEQ ID NO 120
<211> LENGTH: 22
<212> TYPE: DNA
<213> ORGANISM: Artificial Sequence
<220> FEATURE:
<223> OTHER INFORMATION: Primer

<400> SEQUENCE: 120
cgcgatggtt cttcacaatt ca                                            22

<210> SEQ ID NO 121
<211> LENGTH: 21
<212> TYPE: DNA
<213> ORGANISM: Artificial Sequence
<220> FEATURE:
<223> OTHER INFORMATION: Primer

<400> SEQUENCE: 121
acgcgacgct ctaaaggaag t                                             21

<210> SEQ ID NO 122
<211> LENGTH: 20
<212> TYPE: DNA
<213> ORGANISM: Artificial Sequence
<220> FEATURE:
<223> OTHER INFORMATION: Primer

<400> SEQUENCE: 122
ctctcagacc aggcccagca                                               20

<210> SEQ ID NO 123
<211> LENGTH: 20
<212> TYPE: DNA
<213> ORGANISM: Artificial Sequence
<220> FEATURE:
<223> OTHER INFORMATION: Primer

<400> SEQUENCE: 123
gctgaggcaa agcgactcca                                               20

<210> SEQ ID NO 124
<211> LENGTH: 22
<212> TYPE: DNA
<213> ORGANISM: Artificial Sequence
<220> FEATURE:
<223> OTHER INFORMATION: Primer

<400> SEQUENCE: 124
ctctaaagga agtgaccttt ag                                            22

<210> SEQ ID NO 125
<211> LENGTH: 20

<212> TYPE: DNA
<213> ORGANISM: Artificial Sequence
<220> FEATURE:
<223> OTHER INFORMATION: Primer

<400> SEQUENCE: 125
ggctgttact ctcagaccag                                               20

<210> SEQ ID NO 126
<211> LENGTH: 21
<212> TYPE: DNA
<213> ORGANISM: Artificial Sequence
<220> FEATURE:
<223> OTHER INFORMATION: Primer

<400> SEQUENCE: 126
aacctaccga ctgacctgca t                                             21

<210> SEQ ID NO 127
<211> LENGTH: 21
<212> TYPE: DNA
<213> ORGANISM: Artificial Sequence
<220> FEATURE:
<223> OTHER INFORMATION: Primer

<400> SEQUENCE: 127
cctgcatgac gtaggtccac t                                             21

<210> SEQ ID NO 128
<211> LENGTH: 20
<212> TYPE: DNA
<213> ORGANISM: Artificial Sequence
<220> FEATURE:
<223> OTHER INFORMATION: Primer

<400> SEQUENCE: 128
gggtcagatc cgacgtaaag                                               20

<210> SEQ ID NO 129
<211> LENGTH: 19
<212> TYPE: DNA
<213> ORGANISM: Artificial Sequence
<220> FEATURE:
<223> OTHER INFORMATION: Primer

<400> SEQUENCE: 129
gcgtgttccc agccgctag                                                19

<210> SEQ ID NO 130
<211> LENGTH: 20
<212> TYPE: DNA
<213> ORGANISM: Artificial Sequence
<220> FEATURE:
<223> OTHER INFORMATION: Primer

<400> SEQUENCE: 130
gggattggcc gagtcaggtc                                               20

<210> SEQ ID NO 131
<211> LENGTH: 20
<212> TYPE: DNA
<213> ORGANISM: Artificial Sequence
<220> FEATURE:
<223> OTHER INFORMATION: Primer

<400> SEQUENCE: 131
acagagctgc ctgctggagc    20

<210> SEQ ID NO 132
<211> LENGTH: 19
<212> TYPE: DNA
<213> ORGANISM: Artificial Sequence
<220> FEATURE:
<223> OTHER INFORMATION: Primer

<400> SEQUENCE: 132
cggcaagagc tcggtgctc    19

<210> SEQ ID NO 133
<211> LENGTH: 21
<212> TYPE: DNA
<213> ORGANISM: Artificial Sequence
<220> FEATURE:
<223> OTHER INFORMATION: Primer

<400> SEQUENCE: 133
agaacttcgt gggcaggtaa g    21

<210> SEQ ID NO 134
<211> LENGTH: 21
<212> TYPE: DNA
<213> ORGANISM: Artificial Sequence
<220> FEATURE:
<223> OTHER INFORMATION: Primer

<400> SEQUENCE: 134
cgtctgcagg accgcgtttt c    21

<210> SEQ ID NO 135
<211> LENGTH: 19
<212> TYPE: DNA
<213> ORGANISM: Artificial Sequence
<220> FEATURE:
<223> OTHER INFORMATION: Primer

<400> SEQUENCE: 135
agctgatccc gctggtgaa    19

<210> SEQ ID NO 136
<211> LENGTH: 22
<212> TYPE: DNA
<213> ORGANISM: Artificial Sequence
<220> FEATURE:
<223> OTHER INFORMATION: Primer

<400> SEQUENCE: 136
aatggctttg tatcgcacga tg    22

<210> SEQ ID NO 137
<211> LENGTH: 20
<212> TYPE: DNA
<213> ORGANISM: Artificial Sequence
<220> FEATURE:
<223> OTHER INFORMATION: Primer

<400> SEQUENCE: 137
ccactgccgc atccttactc    20

<210> SEQ ID NO 138
<211> LENGTH: 20
<212> TYPE: DNA
<213> ORGANISM: Artificial Sequence -continued

```
<220> FEATURE:
<223> OTHER INFORMATION: Primer

<400> SEQUENCE: 138
cctggtccat ccaccctctg                                              20

<210> SEQ ID NO 139
<211> LENGTH: 19
<212> TYPE: DNA
<213> ORGANISM: Artificial Sequence
<220> FEATURE:
<223> OTHER INFORMATION: Primer

<400> SEQUENCE: 139
tgcccgtcca cgttccaac                                               19

<210> SEQ ID NO 140
<211> LENGTH: 19
<212> TYPE: DNA
<213> ORGANISM: Artificial Sequence
<220> FEATURE:
<223> OTHER INFORMATION: Primer

<400> SEQUENCE: 140
cacggacacc gccactctg                                               19

<210> SEQ ID NO 141
<211> LENGTH: 21
<212> TYPE: DNA
<213> ORGANISM: Artificial Sequence
<220> FEATURE:
<223> OTHER INFORMATION: Primer

<400> SEQUENCE: 141
gagcattggc accctgatt c                                             21

<210> SEQ ID NO 142
<211> LENGTH: 21
<212> TYPE: DNA
<213> ORGANISM: Artificial Sequence
<220> FEATURE:
<223> OTHER INFORMATION: Primer

<400> SEQUENCE: 142
cttacccgtg gtttctgcct g                                            21

<210> SEQ ID NO 143
<211> LENGTH: 21
<212> TYPE: DNA
<213> ORGANISM: Artificial Sequence
<220> FEATURE:
<223> OTHER INFORMATION: Primer

<400> SEQUENCE: 143
agagcattgg caccctgat t                                             21

<210> SEQ ID NO 144
<211> LENGTH: 22
<212> TYPE: DNA
<213> ORGANISM: Artificial Sequence
<220> FEATURE:
<223> OTHER INFORMATION: Primer

<400> SEQUENCE: 144
acttctctta cccgtggttt ct                                           22
```

<210> SEQ ID NO 145
<211> LENGTH: 19
<212> TYPE: DNA
<213> ORGANISM: Artificial Sequence
<220> FEATURE:
<223> OTHER INFORMATION: Primer

<400> SEQUENCE: 145
ctggggccta cgcgaagct                                                19

<210> SEQ ID NO 146
<211> LENGTH: 25
<212> TYPE: DNA
<213> ORGANISM: Artificial Sequence
<220> FEATURE:
<223> OTHER INFORMATION: Primer

<400> SEQUENCE: 146
ctctaaaagt gttacaaaca ttaag                                         25

<210> SEQ ID NO 147
<211> LENGTH: 20
<212> TYPE: DNA
<213> ORGANISM: Artificial Sequence
<220> FEATURE:
<223> OTHER INFORMATION: Primer

<400> SEQUENCE: 147
tggaatcgtg cccggatcag                                               20

<210> SEQ ID NO 148
<211> LENGTH: 26
<212> TYPE: DNA
<213> ORGANISM: Artificial Sequence
<220> FEATURE:
<223> OTHER INFORMATION: Primer

<400> SEQUENCE: 148
tttttggaac gttaaataat ttccta                                        26

<210> SEQ ID NO 149
<211> LENGTH: 22
<212> TYPE: DNA
<213> ORGANISM: Artificial Sequence
<220> FEATURE:
<223> OTHER INFORMATION: Primer

<400> SEQUENCE: 149
cctcagtttc ctcaaaagga at                                            22

<210> SEQ ID NO 150
<211> LENGTH: 20
<212> TYPE: DNA
<213> ORGANISM: Artificial Sequence
<220> FEATURE:
<223> OTHER INFORMATION: Primer

<400> SEQUENCE: 150
cgtgcccgga tcagagcaag                                               20

<210> SEQ ID NO 151
<211> LENGTH: 20
<212> TYPE: DNA
<213> ORGANISM: Artificial Sequence
<220> FEATURE:
<223> OTHER INFORMATION: Primer

<400> SEQUENCE: 151
gcctggaatc gtgcccggat                                                    20

<210> SEQ ID NO 152
<211> LENGTH: 23
<212> TYPE: DNA
<213> ORGANISM: Artificial Sequence
<220> FEATURE:
<223> OTHER INFORMATION: Primer

<400> SEQUENCE: 152
tccaaggaag actaaaaacc cag                                                23

<210> SEQ ID NO 153
<211> LENGTH: 21
<212> TYPE: DNA
<213> ORGANISM: Artificial Sequence
<220> FEATURE:
<223> OTHER INFORMATION: Primer

<400> SEQUENCE: 153
taaaaaccca ggccgggaag c                                                  21

<210> SEQ ID NO 154
<211> LENGTH: 22
<212> TYPE: DNA
<213> ORGANISM: Artificial Sequence
<220> FEATURE:
<223> OTHER INFORMATION: Primer

<400> SEQUENCE: 154
tggtttgttc caaggagtac ag                                                 22

<210> SEQ ID NO 155
<211> LENGTH: 23
<212> TYPE: DNA
<213> ORGANISM: Artificial Sequence
<220> FEATURE:
<223> OTHER INFORMATION: Primer

<400> SEQUENCE: 155
agtacagata gcctttcaa aag                                                 23

<210> SEQ ID NO 156
<211> LENGTH: 23
<212> TYPE: DNA
<213> ORGANISM: Artificial Sequence
<220> FEATURE:
<223> OTHER INFORMATION: Primer

<400> SEQUENCE: 156
agcaaggtga agactaactt ttc                                                23

<210> SEQ ID NO 157
<211> LENGTH: 23
<212> TYPE: DNA
<213> ORGANISM: Artificial Sequence
<220> FEATURE:
<223> OTHER INFORMATION: Primer

<400> SEQUENCE: 157
cttgtacaga atcatcaggc taa                                                23

<210> SEQ ID NO 158

```
<211> LENGTH: 25
<212> TYPE: DNA
<213> ORGANISM: Artificial Sequence
<220> FEATURE:
<223> OTHER INFORMATION: Primer

<400> SEQUENCE: 158
gtccttggag acatctgaga gattc                                        25

<210> SEQ ID NO 159
<211> LENGTH: 20
<212> TYPE: DNA
<213> ORGANISM: Artificial Sequence
<220> FEATURE:
<223> OTHER INFORMATION: Primer

<400> SEQUENCE: 159
gacatctgag agattccggg                                              20

<210> SEQ ID NO 160
<211> LENGTH: 22
<212> TYPE: DNA
<213> ORGANISM: Artificial Sequence
<220> FEATURE:
<223> OTHER INFORMATION: Primer

<400> SEQUENCE: 160
caaagaaagc aaggtgaaga ct                                           22

<210> SEQ ID NO 161
<211> LENGTH: 24
<212> TYPE: DNA
<213> ORGANISM: Artificial Sequence
<220> FEATURE:
<223> OTHER INFORMATION: Primer

<400> SEQUENCE: 161
cagtccttgg agacatctga gaga                                         24

<210> SEQ ID NO 162
<211> LENGTH: 23
<212> TYPE: DNA
<213> ORGANISM: Artificial Sequence
<220> FEATURE:
<223> OTHER INFORMATION: Primer

<400> SEQUENCE: 162
tgaagtgaac tattccttag gtg                                          23

<210> SEQ ID NO 163
<211> LENGTH: 23
<212> TYPE: DNA
<213> ORGANISM: Artificial Sequence
<220> FEATURE:
<223> OTHER INFORMATION: Primer

<400> SEQUENCE: 163
gtctccaagg actgaaataa tgc                                          23

<210> SEQ ID NO 164
<211> LENGTH: 28
<212> TYPE: DNA
<213> ORGANISM: Artificial Sequence
<220> FEATURE:
<223> OTHER INFORMATION: Primer

<400> SEQUENCE: 164
```

```
gagtagcaaa aaatagctga agtgaact                              28

<210> SEQ ID NO 165
<211> LENGTH: 23
<212> TYPE: DNA
<213> ORGANISM: Artificial Sequence
<220> FEATURE:
<223> OTHER INFORMATION: Primer

<400> SEQUENCE: 165
tgacaaccaa tgagtagcaa aaa                                   23

<210> SEQ ID NO 166
<211> LENGTH: 20
<212> TYPE: DNA
<213> ORGANISM: Artificial Sequence
<220> FEATURE:
<223> OTHER INFORMATION: Primer

<400> SEQUENCE: 166
gttgtcagtg tggccagaga                                       20

<210> SEQ ID NO 167
<211> LENGTH: 21
<212> TYPE: DNA
<213> ORGANISM: Artificial Sequence
<220> FEATURE:
<223> OTHER INFORMATION: Primer

<400> SEQUENCE: 167
tgttgtcagt gtggccagag a                                     21
```